US012788998B2

(12) United States Patent
Eby et al.

(10) Patent No.: US 12,788,998 B2
(45) Date of Patent: Nov. 10, 2026

(54) FIXATION MECHANISMS FOR A LEADLESS CARDIAC BIOSTIMULATOR

(71) Applicant: Pacesetter, Inc., Sylmar, CA (US)

(72) Inventors: Thomas B. Eby, Mountain View, CA (US); Christopher R. Jenney, Valencia, CA (US); Craig E. Mar, Fremont, CA (US); Paul M. Paspa, Los Gatos, CA (US)

(73) Assignee: Pacesetter, Inc., Sylmar, CA (US)

( * ) Notice: Subject to any disclaimer, the term of this patent is extended or adjusted under 35 U.S.C. 154(b) by 438 days.

(21) Appl. No.: 18/096,519

(22) Filed: Jan. 12, 2023

(65) Prior Publication Data

US 2023/0158316 A1 May 25, 2023

Related U.S. Application Data

(63) Continuation of application No. 16/541,025, filed on Aug. 14, 2019, now Pat. No. 11,577,086.

(Continued)

(51) Int. Cl.

*A61N 1/37* (2006.01)
*A61N 1/375* (2006.01)
*A61N 1/05* (2006.01)

(52) U.S. Cl.

CPC ..... *A61N 1/37518* (2017.08); *A61N 1/37512* (2017.08); *A61N 1/3756* (2013.01); *A61N 1/0573* (2013.01)

(58) Field of Classification Search

CPC .............. A61N 1/0573; A61N 1/37512; A61N 1/37518; A61N 1/3756

See application file for complete search history.

(56) References Cited

U.S. PATENT DOCUMENTS

| | | | |
|---|---|---|---|
| 3,943,936 | A | 3/1976 | Rasor et al. |
| 3,974,834 | A | 8/1976 | Kane |

(Continued)

FOREIGN PATENT DOCUMENTS

| | | |
|---|---|---|
| EP | 1835962 B1 | 4/2015 |
| EP | 3106201 B1 | 11/2018 |

(Continued)

OTHER PUBLICATIONS

Engineering ToolBox, (2003). Young's Modulus—Tensile and Yield Strength for some common Materials. [online] Available at: https://www.engineeringtoolbox.com/young-modulus-d_417.html [Jul. 8, 2021 ]. (Year: 2003).

*Primary Examiner* — Amanda K Hulbert

(74) *Attorney, Agent, or Firm* — WOMBLE BOND DICKINSON (US) LLP

(57) ABSTRACT

A leadless biostimulator, such as a leadless pacemaker, includes a housing sized and configured to be implanted within a heart of a patient and includes both primary and secondary fixation features. The primary fixation feature is adapted to rotate to fix the leadless biostimulator to a wall of the heart during initial implantation. Once the leadless biostimulator is implanted, the secondary fixation feature is adapted to resist counter-rotation of the leadless biostimulator. The primary fixation feature may include a fixation helix configured to affix the housing to the heart by rotating in a screwing direction. The secondary fixation feature may include an apex to engage the heart to resist unscrewing of the primary fixation feature.

17 Claims, 23 Drawing Sheets

Related U.S. Application Data

(60) Provisional application No. 62/719,954, filed on Aug. 20, 2018.

(56) References Cited

U.S. PATENT DOCUMENTS 4,106,512 A 8/1978 Bisping
4,311,153 A 1/1982 Smits
4,972,848 A 11/1990 Di Domenico et al.
5,003,992 A 4/1991 Holleman et al.
5,076,285 A 12/1991 Hess et al.
5,575,814 A 11/1996 Giele et al.
5,702,437 A 12/1997 Baudino
5,716,391 A 2/1998 Grandjean
5,741,321 A 4/1998 Brennen
5,776,178 A 7/1998 Pohndorf et al.
5,837,006 A 11/1998 Ocel et al.
5,948,015 A 9/1999 Hess et al.
6,489,562 B1 12/2002 Hess et al.
6,556,874 B2 4/2003 Audoglio
6,907,298 B2 6/2005 Smits et al.
6,909,920 B2 6/2005 Lokhoff et al.
6,931,285 B2 8/2005 Bischoff
6,931,286 B2 8/2005 Sigg et al.
7,027,876 B2 4/2006 Casavant et al.
7,082,335 B2 7/2006 Klein et al.
7,103,418 B2 9/2006 Laske et al.
7,127,302 B2 10/2006 Palm
7,158,838 B2 1/2007 Seifert et al.
7,187,971 B2 3/2007 Sommer et al.
7,274,966 B2 9/2007 Sommer et al.
7,313,445 B2 12/2007 McVenes et al.
7,532,939 B2 5/2009 Sommer et al.
7,580,758 B2 8/2009 Junge et al.
7,599,747 B2 10/2009 Feldmann et al.
7,657,325 B2 2/2010 Williams
7,657,326 B2 2/2010 Bodner et al.
7,720,550 B2 5/2010 Sommer et al.
7,751,905 B2 7/2010 Feldmann et al.
7,844,348 B2 11/2010 Swoyer et al.
7,860,580 B2 12/2010 Falk et al.
7,937,148 B2 5/2011 Jacobson
7,937,161 B2 5/2011 Hastings et al.
7,942,917 B2 5/2011 Nowak, Jr.
7,945,333 B2 5/2011 Jacobson
7,967,857 B2 6/2011 Lane
8,010,209 B2 8/2011 Jacobson
8,057,459 B2 11/2011 Rioux et al.
8,135,467 B2 3/2012 Markowitz et al.
8,211,169 B2 7/2012 Lane et al.
8,219,209 B2 7/2012 Amholt et al.
8,219,213 B2 7/2012 Sommer et al.
8,239,039 B2 8/2012 Zarembo et al.
8,313,621 B2 11/2012 Goad et al.
8,346,374 B2 1/2013 Foster et al.
8,352,025 B2 1/2013 Jacobson
8,412,351 B2 4/2013 Zeijlemaker et al.
8,457,742 B2 6/2013 Jacobson
8,478,429 B2 7/2013 Walker et al.
8,478,430 B2 7/2013 Sommer et al.
8,489,205 B2 7/2013 Stotts et al.
8,500,757 B2 8/2013 Miraki et al.
8,527,068 B2 9/2013 Ostroff
8,543,224 B2 9/2013 Foster et al.
8,560,087 B2 10/2013 Foster
8,694,128 B2 4/2014 Seifert et al.
8,755,909 B2 6/2014 Sommer et al.
8,812,134 B2 8/2014 Foster et al.
8,874,232 B2 10/2014 Chen
8,923,985 B2 12/2014 Clark et al.
8,948,883 B2 * 2/2015 Eggen .................. A61N 1/0573 607/119
8,954,168 B2 2/2015 Foster
9,020,611 B2 4/2015 Khairkhahan et al.
9,056,180 B2 6/2015 Powell et al.
9,089,695 B2 7/2015 Seifert et al.
9,186,209 B2 11/2015 Weber et al.
9,216,298 B2 12/2015 Jacobson
9,242,102 B2 1/2016 Khairkhahan et al.
9,272,155 B2 3/2016 Ostroff
9,333,342 B2 5/2016 Haasl et al.
9,333,344 B2 5/2016 Foster
9,358,387 B2 * 6/2016 Suwito ................... A61N 1/057
9,358,400 B2 6/2016 Jacobson
9,421,384 B2 8/2016 Taff et al.
9,517,336 B2 12/2016 Eggen et al.
9,579,500 B2 2/2017 Rys et al.
9,682,230 B2 6/2017 Zhang et al.
9,694,172 B2 * 7/2017 Foster .................... A61N 1/059
9,724,126 B2 8/2017 Gerber et al.
9,770,586 B2 9/2017 Doerr et al.
9,775,982 B2 10/2017 Grubac et al.
9,808,617 B2 11/2017 Ostroff et al.
9,827,414 B2 11/2017 Doerr et al.
9,867,964 B2 1/2018 Drake et al.
9,899,778 B2 2/2018 Hanson et al.
9,907,952 B2 3/2018 Sommer et al.
9,907,953 B2 3/2018 Orts et al.
9,943,682 B2 4/2018 Eggen et al.
10,028,832 B2 7/2018 Quill et al.
10,046,167 B2 8/2018 Schmidt et al.
10,071,243 B2 9/2018 Kuhn et al.
10,080,887 B2 9/2018 Schmidt et al.
10,092,744 B2 10/2018 Sommer et al.
10,099,050 B2 10/2018 Chen et al.
2003/0065374 A1 4/2003 Honeck
2003/0114908 A1 6/2003 Flach
2004/0102830 A1 5/2004 Williams
2006/0020317 A1 1/2006 Flach et al.
2009/0118776 A1 5/2009 Kelsch et al.
2009/0234368 A1 9/2009 Gore
2011/0251660 A1 * 10/2011 Griswold ........... A61N 1/37205 607/126
2012/0116489 A1 * 5/2012 Khairkhahan ..... A61N 1/37518 607/127
2013/0331920 A1 12/2013 Osypka
2015/0025350 A1 1/2015 Schnittker
2015/0051612 A1 2/2015 Schmidt et al.
2015/0051614 A1 2/2015 Schmidt et al.
2015/0374976 A1 * 12/2015 Régnier ............. A61N 1/37205 219/121.64
2016/0051811 A1 * 2/2016 Doerr ..................... A61N 1/059 606/191
2016/0331325 A1 11/2016 Munsinger et al.
2016/0354600 A1 12/2016 Kolberg et al.
2017/0043155 A1 2/2017 Marshall et al.
2017/0072191 A1 * 3/2017 Ma ....................... A61N 1/3756
2017/0119555 A1 5/2017 Bayer
2017/0120042 A1 5/2017 Becker et al.
2017/0165454 A1 6/2017 Tuohy et al.
2017/0189669 A1 7/2017 Kamarajugadda et al.
2017/0239464 A1 8/2017 Taeubert et al.
2017/0252035 A1 9/2017 Miraki
2018/0071543 A1 3/2018 Taff et al.
2018/0133464 A1 5/2018 Taeubert et al.
2018/0207434 A1 7/2018 Webb et al.
2018/0221014 A1 8/2018 Darabian
2018/0236244 A1 8/2018 Stevenson et al.
2019/0076664 A1 * 3/2019 Ollivier .............. A61N 1/37518
2019/0366098 A1 * 12/2019 Bockeria .............. A61N 1/3756

FOREIGN PATENT DOCUMENTS

WO 2006045073 A1 4/2006
WO 2007047681 A2 4/2007
WO 2012051235 A1 4/2012

* cited by examiner

FIXATION MECHANISMS FOR A LEADLESS CARDIAC BIOSTIMULATOR

This application is a continuation of co-pending U.S. patent application Ser. No. 16/541,025, filed on Aug. 14, 2019, which claims the benefit of U.S. Provisional Patent Application No. 62/719,954, filed on Aug. 20, 2018, and these applications are incorporated herein by reference in their entirety to provide continuity of disclosure.

FIELD

The present disclosure relates to leadless cardiac pacemakers and similar biostimulators, and more particularly, to features and methods by which such biostimulators are affixed within a heart. More specifically, the present disclosure relates to features and methods for resisting dislodgment of a leadless biostimulator following implantation within the heart.

BACKGROUND

Cardiac pacing by an artificial pacemaker or similar leadless biostimulator provides an electrical stimulation to the heart when a natural pacemaker and/or conduction system of the heart fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

SUMMARY OF THE DESCRIPTION

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional systems relate to the separately implanted pulse generator and pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the related applications cited below in the Detailed Description.

The problematic aspects of conventional systems described above have been addressed by self-contained or leadless pacemakers or other biostimulators. Such biostimulators are typically fixed to an intracardial implant site by an actively engaging mechanism such as a screw or helical member that screws into the myocardium. There is a need in the art, however, for improved leadless biostimulator fixation features.

In a first embodiment of the present disclosure, a leadless biostimulator is provided. The leadless biostimulator includes a housing sized and configured to be implanted within a heart of a patient, a primary fixation feature attached to the housing and configured to affix the housing to a wall of the heart by rotating in a screwing direction, and a secondary fixation feature disposed on, mounted on, or otherwise coupled to the primary fixation feature. The secondary fixation feature includes a sleeve disposed about the primary fixation feature. The sleeve has an outer surface tapering radially outward to an apex. For example, the sleeve can include a barb, e.g., a flexible barb, extending from a first end of the sleeve to a barb tip at the apex. The flexible barb is angled in a direction opposite the screwing direction of the primary fixation feature such that rotation of the primary fixation feature in an unscrewing direction causes the flexible barb to engage the wall of the heart so as to reduce a likelihood that the primary fixation device will disengage from the wall of the heart.

In certain implementations, the secondary fixation feature may be formed from one or more materials including polyimide, polyester, polyethylene, polypropylene, polyurethane, polyether ether ketone (PEEK), or polyvinylidene fluoride. In another implementation, the secondary fixation feature may be formed from a material having a Young's modulus from and including 0.5 gigapascals (GPa) to and including 10 GPa.

In certain implementations, the secondary fixation feature may be formed from one or more bioabsorbable materials. For example, the bioabsorbable material(s) may include a magnesium alloy, a polyglycolide (PGA), polylactide (PLA), or a combination bioabsorbable material such as Vicryl® (PGA-LPLA).

In another implementation, the flexible barb of the secondary fixation feature is one of several flexible barbs. Each of the barbs may similarly extend from the sleeve and be angled in the direction opposite the screwing direction of the primary fixation feature. For example, in some implementations, the several flexible barbs may include four barbs. Regardless of the number of barbs, each barb may be from and including 0.010 inches to and including 0.200 inches in length.

In certain implementations, the secondary fixation feature is formed directly onto the primary fixation feature. Alternatively, the secondary fixation feature is formed separately from the primary fixation feature and adhered to the primary fixation feature.

The sleeve of the secondary fixation feature may generally include a first end and a second end opposite the first end. The outer surface may extend and taper from the first end, e.g., the flexible barb can extend from the first end, and the second end can have a taper. The sleeve may also have a thickness from and including 0.001 inches to and including 0.010 inches.

In certain implementations, the primary fixation feature is a helical wire having several turns and the secondary fixation feature is disposed or mounted on a first distal turn of the helical wire.

In another embodiment of the present disclosure, a leadless biostimulator is provided. The leadless biostimulator includes a primary fixation feature attached to a distal end of the leadless biostimulator and configured to affix the leadless biostimulator to a wall of a heart by rotating in a screwing direction. The leadless biostimulator further includes a secondary fixation feature coupled to the primary fixation feature. The secondary fixation feature is configured such that, when implanted within the wall of the heart, a first torque opposite the screwing direction causes the secondary fixation feature to engage the wall of the heart, thereby providing a first resistance to rotation of the leadless biostimulator in the direction opposite the screwing direction. The secondary fixation feature is further configured such that, when implanted within the wall of the heart, a second torque opposite the screwing direction and greater than the first torque causes deformation of the secondary fixation feature such that the secondary fixation feature is at least partially disengaged from the wall of the heart, thereby providing a second resistance less than the first resistance to rotation of the leadless biostimulator in the direction opposite the screwing direction.

In certain implementations, the first torque is up to and including 0.5 ounce-inches (oz-in) and the second torque is from and including 0.5 oz-in to and including 2.0 oz-in. Such values for the first torque and the second torque are offered by way of example only. In an embodiment, the second torque is higher than the first torque, and may be higher by a scale factor. The scale factor can be a multiplier that provides more resistance to disengagement under torque. For example, the scale factor may be at least five, e.g., the second torque may be at least 5 times the first torque. In an embodiment, scale factor is ten or more, e.g., the second torque is 10 times the first torque.

In another implementation, the secondary fixation feature includes one or more flexible barbs extending in the direction opposite the screwing direction and the deformation of the secondary fixation feature includes a deformation of the one or more flexible barbs. In such cases, the one or more flexible barbs may extend from a first end of the secondary fixation feature and the secondary fixation feature may further include a tapered surface on a second end opposite the first end.

In another aspect of the present disclosure a leadless biostimulator is provided that includes a housing sized and configured to be implanted within a heart of a patient and a planar fixation feature coupled to the housing. The planar fixation feature includes several arms extending along a lateral plane of the housing. For example, the arms can extend to a lateral location that is radially outward (radially more distant) from a primary fixation feature. Each arm includes a primary fixation feature configured to affix the housing to a wall of the heart by rotating the housing in a screwing direction and a secondary fixation feature configured to engage the wall of the heart to resist rotation of the housing in a direction opposite the screwing direction.

In certain implementations, the arms include from and including two arms to and including six arms. Each of the arms may extend along a circular, spiral, or straight path along the lateral plane.

The planar fixation feature may be formed from a unitary sheet, such as by at least one of trimming, die cutting, or laser cutting the unitary sheet. The unitary sheet may have a thickness from and including 0.001 inches to and including 0.02 inches and may be formed from at least one of polyimide, polyester, polyethylene, polypropylene, polyurethane, polyether ether ketone (PEEK), or polyvinylidene fluoride.

The secondary fixation feature may be a barb disposed at an end of each arm. The barbs may, in certain implementations, have a length from and including 0.01 inches to and including 0.05 inches. The barbs may also have a width from and including 0.01 inches to and including 0.05 inches.

The leadless biostimulator may further include a distal cap coupled to a distal end of the housing such that the planar fixation feature is disposed between the distal cap and the housing. In such implementations, the distal end of the housing may include a distal protrusion and each of the planar fixation feature and the cap may define respective through holes. The planar fixation feature and the distal cap may then be coupled to the housing, at least in part, by disposing the distal protrusion through each of the respective through holes.

Each arm of the several arms may be configured to resist rotation of the housing in the direction opposite the screwing direction when a first torque is applied in the direction opposite the screwing direction and to deform when a second torque is applied in the direction opposite the screwing direction. The second torque may be greater than the first torque. The first torque may, in some cases, be up to and including 0.5 oz-in. The second torque may, in some cases, be from and including 0.5 oz-in to and including 2.0 oz-in. To facilitate flexing and deformation of the arms, the planar fixation feature may be formed from a material having a Young's modulus from and including 0.5 GPa to and including 10 GPa.

In another aspect of the present disclosure a leadless biostimulator is provided that includes a housing sized and configured to be implanted within a heart of a patient and defining a longitudinal axis and a planar fixation feature extending along a plane lateral to the housing. The planar fixation feature is adapted to engage a wall of the heart when rotated in a first direction and, when engaged with the wall of the heart, to resist disengagement of the wall of the heart when rotated in a second direction opposite the first direction.

In certain implementations, the planar fixation feature may be configured such that, when engaged with the wall of the heart, a first torque in the second direction causes the planar fixation feature to engage the wall of the heart, thereby providing a first resistance to rotation of the leadless biostimulator in the second direction. The planar fixation feature may be further configured such that, when engaged with the wall of the heart, a second torque in the second direction, which is greater than the first torque causes deformation of the planar fixation feature such that the planar fixation feature is at least partially disengaged from the wall of the heart. By doing so, a second resistance to rotation is provided that is less than the first resistance to rotation of the leadless biostimulator in the direction opposite the screwing direction. The first torque may, in some cases, be up to and including 0.5 oz-in. The second torque may, in some cases, be from and including 0.5 oz-in to and including 2.0 oz-in.

In another aspect of the present disclosure, a leadless biostimulator is provided that includes a housing sized and configured to be implanted within a heart of a patient and defining a longitudinal axis and a fixation feature coupled to the housing. The fixation feature includes several arms, each arm of the several arms extending distally about the longitudinal axis. Each arm includes a primary fixation feature configured to affix the housing to a wall of the heart by rotating the housing in a screwing direction and a secondary fixation feature configured to engage the wall of the heart and to resist rotation of the housing in a direction opposite the screwing direction. In certain implementations, the arms include from and including two arms to and including four arms.

The planar fixation feature may be formed from a unitary tube, such as by at least one of trimming, die cutting, or laser cutting the unitary tube. In certain implementations, the unitary tube may have a thickness from and including 0.004 inches to and including 0.020 inches. The unitary tube may be formed from at least one of polyimide, polyester, polyethylene, polypropylene, polyurethane, polyether ether ketone (PEEK), or polyvinylidene fluoride.

In certain implementations, the secondary fixation feature is a barb disposed at an end of the arm. In such cases, the barb may have a length from and including 0.010 inches to and including 0.200 inches. The barb may also have a thickness from and including 0.010 inches to and including 0.200 inches.

Each of the arms may, in certain implementations extend distally about the longitudinal axis at a pitch angle up to 90 degrees.

The leadless biostimulator may further include a distal header assembly including a header body extending along the longitudinal axis and the fixation feature, with the fixation feature disposed about the header body.

In another implementation, each arm of the several arms is configured to resist rotation of the housing in the direction opposite the screwing direction when a first torque is applied in the direction opposite the screwing direction and to deform when a second torque is applied in the direction opposite the screwing direction, the second torque being greater than the first torque. In such implementations, the first torque may be, in some cases, up to and including 0.5 oz-in. The second torque may, in some cases, be from and including 0.5 oz-in to and including 2.0 oz-in. To facilitate deformation of the arms, the fixation feature may be formed from a material having a Young's modulus from and including 0.5 GPa to and including 10 GPa.

In yet another aspect of the present disclosure, a leadless biostimulator is provided that includes a housing sized and configured to be implanted within a heart of a patient and defining a longitudinal axis and a fixation feature extending from a distal end of the housing. The fixation feature includes several arms extending about the longitudinal axis, each of the arms configured to engage a wall of the heart when rotated in a first direction and, when implanted, to resist rotation in a second direction opposite the first direction. The fixation feature is configured such that, when engaged with the wall of the heart, a first torque in the second direction causes the fixation feature to engage the wall of the heart, thereby providing a first resistance to rotation of the leadless biostimulator in the second direction. The fixation feature is further configured such that, when engaged with the wall of the heart, a second torque in the second direction and greater than the first torque causes deformation of the fixation feature such that the fixation feature is at least partially disengaged from the wall of the heart, thereby providing a second resistance less than the first resistance to rotation of the leadless biostimulator in the second direction.

In certain implementations, the first torque may, in some cases, be up to and including 0.5 oz-in. The second torque may, in some cases, be from and including 0.5 oz-in to and including 2.0 oz-in. Each arm of the several arms may include a tip that extends, at least in part, in the first direction and a barb that extends, at least in part, in the second direction. Also, the fixation feature may be formed from a unitary tubular structure.

In yet another aspect of the present disclosure, a leadless biostimulator is provided that includes a housing sized and configured to be implanted within a heart of a patient and defining a longitudinal axis. The leadless biostimulator further includes a primary fixation feature attached to the housing and configured to affix the housing to a wall of the heart by rotating in a screwing direction and an anti-unscrewing feature. The anti-unscrewing feature includes a planar arm disposed proximal to at least a portion of the primary fixation feature and extending laterally relative to the longitudinal axis. The planar arm extends in a direction opposite the screwing direction of the primary fixation feature such that rotation of the primary fixation helix in an unscrewing direction causes the planar arm to engage the wall of the heart so as to prevent the primary fixation feature from disengaging the wall of the heart.

In some implementation the planar arm is one of several planar arms, each of the planar arms disposed proximal to at least a portion of the primary fixation feature and extending laterally relative to the longitudinal axis.

In certain implementations, the planar arm may conform to various predefined dimensions. For example, the planar arm may have a thickness from and including 0.001 inches to and including 0.02 inches. As another example, the planar arm may have a length from and including 0.002 inches to and including 0.01 inches. As yet another example, the planar arm may have a width from and including 0.001 inches to and including 0.005 inches. The planar arm may also be formed from materials having particular predetermined properties. For example, the planar arm may be formed from a material having a Young's modulus from and including 0.5 GPa to and including 10 GPa.

The leadless biostimulator may have a header assembly that includes a header body, a header cap coupled to a distal end of the header body and a shim disposed between the header body and the header cap and that includes the planar arm. The shim may, in certain implementations, be formed from one of several materials. For example, the shim can be formed from flexible biocompatible materials including, without limitation, one or more of polyimide, polyester, polyethylene, polypropylene, polyurethane, polyether ether ketone (PEEK), or polyvinylidene fluoride. Alternatively, the shim can be formed from a bioresorbable polymer such as polyglycolide (PGA), polylactide (PLA), polycaprolactone (PCL), polydioxanone (PDO), polytrimethylene carbonate (TMC), and co-polymers thereof, or bioresorbable metals such as magnesium alloys, iron alloys, zinc alloys, and combinations thereof.

The shim may include a circular body having an outer edge and the planar arm may extend from the outer edge of the circular body. For example, the planar arm may extend from a point on the outer edge located at an intersection between the outer edge and a line extending tangentially from a circle having a radius extending from a center of the circular body. The radius may, in certain implementations, be from and including 0.050 inches to and including 0.0100 inches. In certain implementations, the planar arm may extend from the outer edge along the tangential line. Alternatively, the planar arm may extend from the outer edge at an angle relative to the tangential line.

The leadless biostimulator may include an additional planar arm extending from the outer edge of the circular body. In such implementations, the second planar arm may be offset along the outer edge by an angle from and including 90 degrees to and including 270 degrees relative to the first planar arm.

In another aspect of the present disclosure a leadless biostimulator is provided that includes a housing sized and configured to be implanted within a heart of a patient and defining a longitudinal axis. The leadless biostimulator further includes a primary fixation feature attached to the housing and configured to affix the housing to a wall of the heart by rotating in a screwing direction and a header assembly disposed at a distal end of the housing. The header assembly includes a header body, a header cap coupled to a distal end of the header body, and a shim disposed between the header body and the header cap, the shim including several laterally extending planar arms extending opposite the screwing direction of the primary fixation feature.

In certain implementations, the shim includes one of a shim notch or a shim protrusion that mates with a corresponding header body protrusion or a header body notch, respectively, to align the shim relative to the primary fixation feature.

In another implementations, the primary fixation feature is a fixation helix coupled to and extending distally from the header body. In such implementations, the shim is disposed such that each planar arm of the planar arms extends between a respective pair of adjacent turns of the fixation helix.

The shim may have a thickness from and including 0.001 inches to and including 0.02 inches and may be formed from a converted film. The shim may also be formed from one or more of polyimide, polyester, polyethylene, polypropylene, polyurethane, polyether ether ketone (PEEK), or polyvinylidene fluoride.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
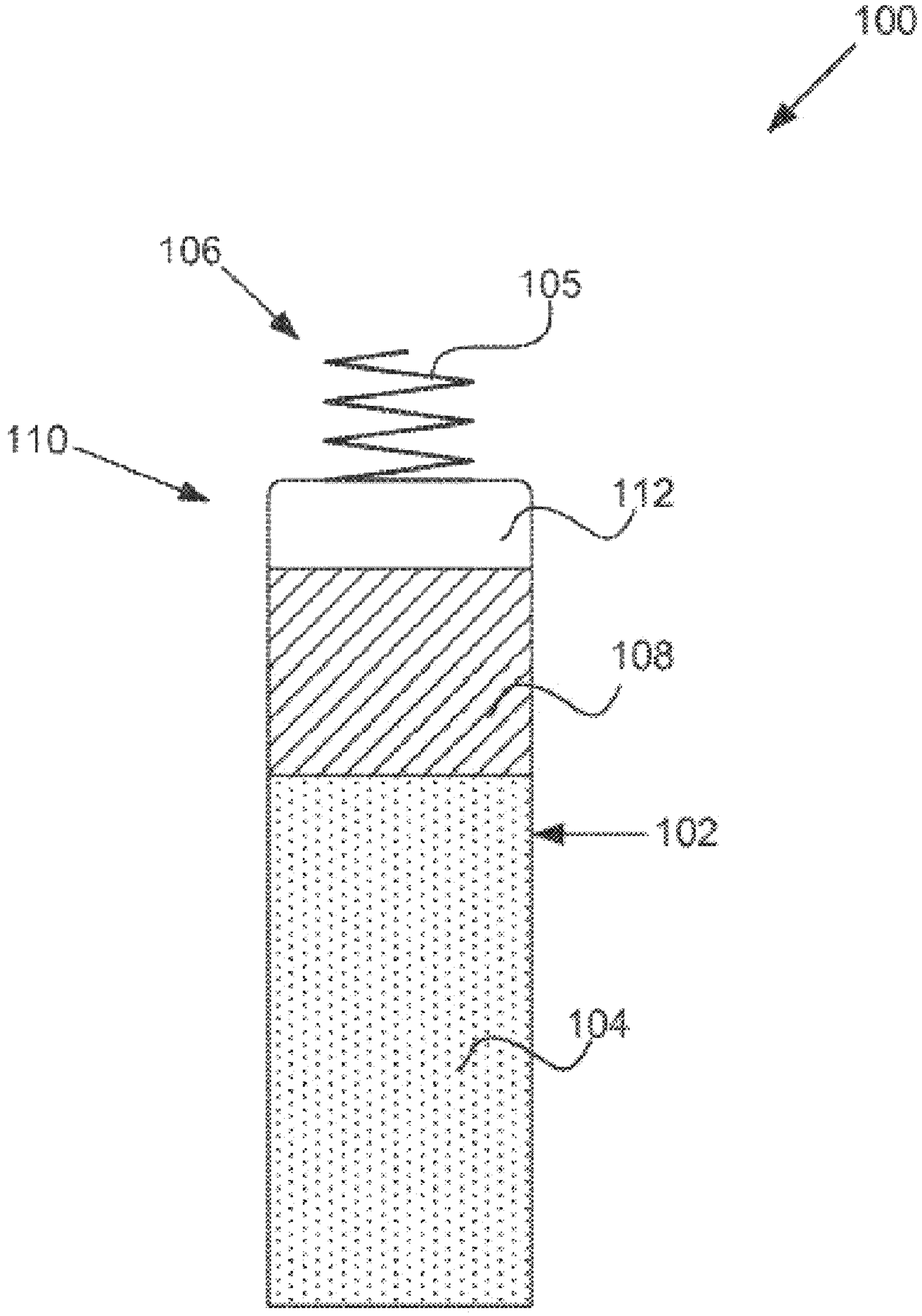
FIG. 1 illustrates a leadless cardiac pacemaker or biostimulator, in accordance with an embodiment.

The following detailed description refers to the accompanying drawings that illustrate exemplary embodiments. Other embodiments are possible, and modifications may be made to the disclosed embodiments within the spirit and scope of the invention. Therefore, the following detailed description is not meant to limit the invention. Rather, the scope of the invention is defined by the appended claims.

Various embodiments of a system including one or more leadless cardiac pacemakers or biostimulators are described.

An embodiment of a cardiac pacing system configured to attain these characteristics includes a leadless cardiac pacemaker that is substantially enclosed in a hermetic housing suitable for placement on or attachment to the inside or outside of a cardiac chamber. The pacemaker can have two or more electrodes located within, on, or near the housing, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a cardiac pacemaker can be adapted for implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Self-contained or leadless pacemakers or other biostimulators are typically fixed to an intracardial implant site by an actively engaging mechanism such as a screw or helical member that screws into the myocardium. Examples of such leadless biostimulators are described in the following publications, the disclosures of which are incorporated by reference: (1) U.S. application Ser. No. 11/549,599, filed on Oct. 13, 2006, entitled "Leadless Cardiac Pacemaker System for Usage in Combination with an Implantable Cardioverter-Defibrillator", and issued as U.S. Pat. No. 8,457,742 on Jun. 4, 2013; (2) U.S. application Ser. No. 11/549,581 filed on Oct. 13, 2006, entitled "Leadless Cardiac Pacemaker", and issued as U.S. Pat. No. 9,358,400 on Jun. 7, 2016; (3) U.S. application Ser. No. 11/549,591, filed on Oct. 13, 2006, entitled "Leadless Cardiac Pacemaker System with Conductive Communication" and issued as U.S. Pat. No. 9,216,298 on Dec. 22, 2015; (4) U.S. application Ser. No. 11/549,596 filed on Oct. 13, 2006, entitled "Leadless Cardiac Pacemaker Triggered by Conductive Communication" and issued as U.S. Pat. No. 8,352,025 on Jan. 8, 2013; (5) U.S. application Ser. No. 11/549,603 filed on Oct. 13, 2006, entitled "Rate Responsive Leadless Cardiac Pacemaker" and issued as U.S. Pat. No. 7,937,148 on May 3, 2011; (6) U.S. application Ser. No. 11/549,605 filed on Oct. 13, 2006, entitled "Programmer for Biostimulator System" and issued as U.S. Pat. No. 7,945,333 on May 17, 2011; (7) U.S. application Ser. No. 11/549,574, filed on Oct. 13, 2006, entitled "Delivery System for Implantable Biostimulator" and issued as U.S. Pat. No. 8,010,209 on Aug. 30, 2011; and (8) International Application No. PCT/US2006/040564, filed on Oct. 13, 2006, entitled "Leadless Cardiac Pacemaker and System" and published as WO07047681A2 on Apr. 26, 2007.

FIG. 1 shows a leadless cardiac pacemaker or leadless biostimulator 100. The biostimulators can include a hermetic housing 102 with electrodes 104 and 106 disposed thereon. As shown, electrode 106 can be disposed on or integrated within a fixation device 105, and the electrode 104 can be disposed on the housing 102. The fixation device 105 can be a fixation helix or other flexible or rigid structure suitable for attaching the housing to tissue, such as heart tissue. In other embodiments, the electrode 106 may be independent from the fixation device in various forms and sizes. The housing can also include an electronics compartment 110 within the housing that contains the electronic components necessary for operation of the biostimulator. The hermetic housing can be adapted to be implanted on or in a human heart, and can be cylindrically shaped, rectangular, spherical, or any other appropriate shapes, for example.

The housing can include a conductive, biocompatible, inert, and anodically safe material such as titanium, 316L stainless steel, or other similar materials. The housing can further include an insulator disposed on the conductive material to separate electrodes 104 and 106. The insulator can be an insulative coating on a portion of the housing between the electrodes, and can include materials such as silicone, polyurethane, parylene, or another biocompatible electrical insulator commonly used for implantable medical devices. In the embodiment of FIG. 1, a single insulator 108 is disposed along the portion of the housing between electrodes 104 and 106. In some embodiments, the housing itself can include an insulator instead of a conductor, such as an alumina ceramic or other similar materials, and the electrodes can be disposed upon the housing.

As shown in FIG. 1, the biostimulator can further include a header assembly 112 to isolate electrode 104 from electrode 106. The header assembly 112 can be made from tecothane or another biocompatible plastic, and can contain a ceramic to metal feedthrough, a glass to metal feedthrough, or other appropriate feedthrough insulator as known in the art.

The electrodes 104 and 106 can include pace/sense electrodes, or return electrodes. A low-polarization coating can be applied to the electrodes, such as platinum, platinum-iridium, iridium, iridium-oxide, titanium-nitride, carbon, or other materials commonly used to reduce polarization effects, for example. In FIG. 1, electrode 106 can be a pace/sense electrode and electrode 104 can be a return electrode. The electrode 104 can be a portion of the conductive housing 102 that does not include an insulator 108.

Several techniques and structures can be used for attaching the housing 102 to the interior or exterior wall of the heart. A helical fixation device 105, can enable insertion of the device endocardially or epicardially through a guiding catheter. A torqueable catheter can be used to rotate the housing and force the fixation device into heart tissue, thus affixing the fixation device (and also the electrode 106 in FIG. 1) into contact with stimulable tissue. Electrode 104 can serve as an indifferent electrode for sensing and pacing. The fixation device may be coated partially or in full for electrical insulation, and a steroid-eluting matrix may be included on or near the device to minimize fibrotic reaction, as is known in conventional pacing electrode-leads.

Various anti-unscrewing features (also referred to herein as secondary fixation features or mechanisms) can be included on the biostimulator to provide a feature that requires that the torque necessary to unscrew the biostimulator from tissue is greater than the torque necessary to unscrew the biostimulator without such a feature. In some embodiments, the torque necessary to unscrew the biostimulator from tissue is greater than the torque necessary to further screw, engage, or re-engage the biostimulator into tissue. When an anti-unscrewing feature provides this function, the chances of a biostimulator accidentally unscrewing or disengaging itself from the tissue is reduced. It should be noted that the torque necessary to initially insert a biostimulator into tissue is greater due to the puncturing or piercing of tissue and the formation of a helical cavity. Thus, in some embodiments, the anti-unscrewing features need only provide that the torque necessary to unscrew the biostimulator from tissue be greater than the torque necessary to unscrew the biostimulator from tissue after the biostimulator has already been implanted in tissue (i.e., after the tissue has been pierced).

Figure 2:
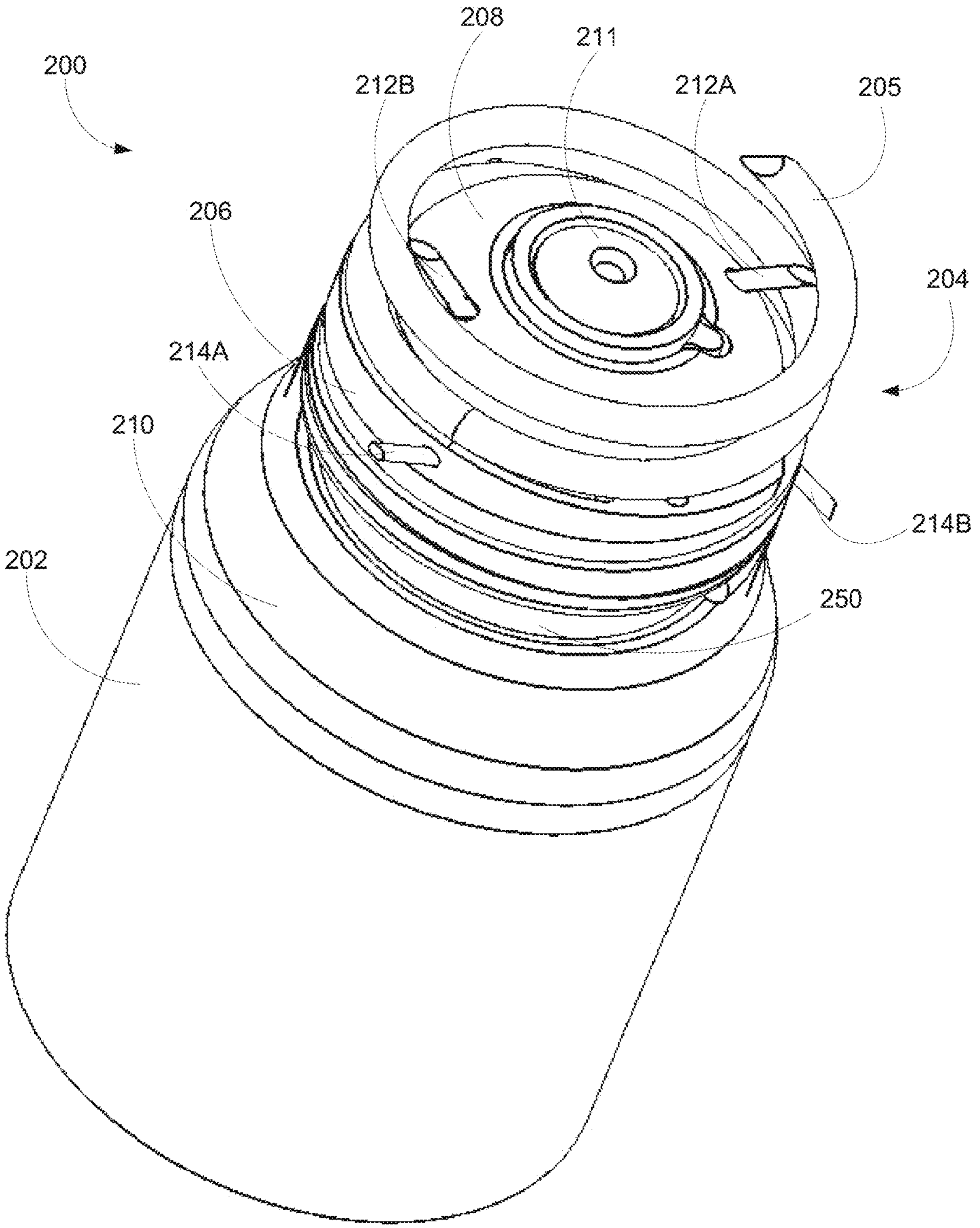
FIG. 2 is an isometric view of a first biostimulator, in accordance with an embodiment.

FIG. 2 is an isometric view of a biostimulator 200 in accordance with the present disclosure. The biostimulator 200 includes a housing 202 and a header assembly 204 coupled thereto. Coupling of the housing 202 to the header assembly 204 may be accomplished in various ways including, without limitation, one or more of a biocompatible adhesive, a threaded connection, and ultrasonic welding.

The header assembly 204 generally includes a primary fixation device 205 and one or more forward facing anti-unscrewing features 212A, 212B. More specifically, the primary fixation device 205 can be a primary helix 205 pointing in a first direction, and the forward facing anti-unscrewing features 212A, 212B can be several forward facing sutures 212A, 212B extending from a forward face of the biostimulator 200 in a second direction opposite the first direction.

The primary helix 205 may be a helical wire. The helical wire can be a wire substantially formed of any suitable biocompatible material including, without limitation, one or more of stainless steel, nickel-titanium alloys (such as Nitinol), nickel-chromium allows (such as Incoloy®), titanium, or multiphase nickel alloys (such as MP35N®). In certain implementations, the substrate material of the primary helix 205 may also be conductive such that the primary helix 205 may be used as an electrode for sensing and/or pacing of cardiac tissue.

The primary helix 205 is preferably sized to couple the biostimulator 200 to cardiac tissue while minimizing damage to the cardiac tissue. In certain implementations, for example, the primary helix 205 extends from and including 0.25 turns to and including 3 turns from the helix mount 206, has a wire diameter from and including 0.003 inches to and including 0.03 inches, has a pitch diameter from and including 0.06 inches to and including 0.3 inches, and has a pitch from and including 0.01 inches to and including 0.05 inches. While the implementations illustrated herein include a single primary helix 205, other implementations of the present disclosure may include multiple fixation helices, each extending in the same direction and each adapted to engage cardiac tissue in response to rotation of the biostimulator 200. Such multi-helix implementations may include biostimulators with multifilar helices in which multiple wires are conjoined, e.g., jointly wound, or biostimulators including multiple offset helices.

Functionality of the sutures 212A, 212B depends, at least in part, on their flexibility. Suture flexibility may be controlled by, among other things, material selection, and suture dimensions while the overall counter rotational resistance provided by the forward facing sutures may be further modified by, among other things, the quantity of sutures employed and the positioning of the sutures relative to each other or relative to the primary helix 205. Regarding materials, the sutures 212A, 212B may be formed of various flexible biocompatible materials including, without limitation, one or more of polypropylene, polyethylene, polyester, nylon, polyurethane, silicone, poly(lactic acid) (PLA), poly (glycolic acid) (PGA), polyimide, polyether ether ketone (PEEK), and polycarbonate. Other biocompatible materials that may be used to form the sutures 212A, 212B include natural materials including one or more of hair, horse hair, nail, hide, horn, or plant fibers, such as horsetail or thistle.

Dimensionally, the length and diameter of the sutures 212A, 212B may vary depending on the specific configuration of the biostimulator 200, however, in certain implementations the sutures 212A, 212B have a length from and including 0.003 inches to and including 0.2 inches and a diameter from and including 0.003 inches to and including 0.03 inches. In certain implementations, the flexibility of the sutures 212A, 212B is sufficiently high to resist counter rotation caused by general cardiac activity and movement of the patient, but low enough such that removal and/or repositioning of the biostimulator 200 is possible without significant damage to the cardiac tissue. For example, each of the sutures 212A, 212B may have a stiffness (Young's Modulus) from and including 0.5 gigapascals (GPa) to and including 10 GPa. In certain implementations, the sutures 212A, 212B may include tips that are configured to improve engagement with cardiac tissue. For example, the suture 212A, 212B may be trimmed or otherwise formed to have sharpened tips.

The header assembly 204 may include multiple components including a helix mount 206, a cap 208, and a flange 210. Generally, the helix mount 206 couples to and retains the primary helix 205 while the cap 208 retains each of the forward facing sutures. The flange 210 couples the header assembly 204 to the housing 202 and provides a central structure to which each of the helix mount 206 and the cap 208 are mounted. The flange 210 may further include an electrode 211 that contacts tissue when the biostimulator is implanted and through which electrical stimulation may be delivered. The example biostimulator 200 further includes several laterally extending anti-unscrewing features in the form of lateral sutures 214A-214C (lateral 214C being hidden in FIG. 2). As illustrated in FIG. 2, such lateral sutures may be coupled to and extend from the helix mount 206.

Portions of the header assembly 204 may be coated or filled with a biocompatible epoxy or similar material. For example, in certain implementations, a gap 250 may be present between the flange 210 and the helix mount 206 and may be filled with a biocompatible adhesive or epoxy such as one of NuSil™ medical adhesive 6219 and Hysol® M31-CL. Such adhesives and epoxies may be used to reinforce coupling between components of the header assembly 204 and protect the components from wear and corrosion.

One or more surface modification technologies may also be applied to contact surfaces of the biostimulator 200. In general, such contact surfaces may correspond to any component of the biostimulator 200 that contacts or otherwise interacts with tissue of the heart when the biostimulator 200 is implanted. Examples of contact surfaces of the biostimulator 200 include, without limitation, the face of the cap 208 and the exterior surface of the primary helix 205. For example, a surface modification treatment may be applied to the cap 208, in whole or in part (e.g., only a specific portion of the face 208), to modify the properties of the cap 208 as compared to the substrate from which the cap 208 is substantially formed.

Such technologies may include technologies to, among other things, change one or more of the surface energy, the surface charge, the surface chemistry, or the surface morphology of the contact surface. Such modifications may be applied to promote a more organized, thinner fibrous capsule forming about the contact surface when the biostimulator 200 is implanted, thereby reducing the effects of such a capsule on pacing thresholds. For example, implantation of the biostimulator 200 into the heart may cause the body's natural foreign body response (FBR) to form thick scar tissue around or near a distal end of the biostimulator 200 or around specific components of the biostimulator 200, such as the cap 208 and the primary helix 205. This scar tissue may ultimately impede pacing by the biostimulator 200. By altering the properties of the contact surface between the biostimulator 200 (or a specific component thereof) and the heart through the application of surface modification technologies, the FBR may be controlled or directed to promote a more predictable tissue reaction. For example, surface modification technologies may be applied to promote the formation of a relatively thin and even tissue capsule around the biostimulator 200. Surface modification may also be used to promote improved substrate-to-tissue adhesion, thereby improving fixation of the biostimulator 200 within the heart tissue.

Various surface modification technologies may be applied to the contact surface using different techniques. For example, surface energy of the contact surface may be modified by, among other things, glow discharge or plasma treatment of the contact surface. As another example, surface charge may be modified by material selection or deposition of polymers or other materials that may be electrically charged or conductive onto the contact surface. Examples of such materials include, without limitation, piezoelectric polymer films and polyvinylidene fluoride (PVDF) films. Surface chemistry may be modified by, among other techniques, one or more of radiation grafting, protein patterning with soft lithography or micro-contact printing, and immobilization of peptides or proteins in specific micro patterns on the material surface. As yet another example, surface morphology may be modified by topographical patterning of the contact surface. Such patterning techniques may include, without limitation, one or more of laser micromachining and micromolding, such as micromolding using polydimethylsiloxane (PDMS).

As described above, biostimulators in accordance with this disclosure can include one or more sutures disposed on a forward face of the biostimulator adjacent a primary fixation feature, such as a helical screw. The sutures can be oriented in a direction opposite the primary fixation feature such that after fixation of the biostimulator by rotation in a first direction, counter rotation causes the sutures to engage tissue adjacent to the primary fixation feature, thereby resisting further counter rotation. In certain implementations, the sutures are formed of a flexible material such that sufficient counter torque applied to the biostimulator may cause the sutures to bend and disengage from the tissue adjacent to the primary fixation. As a result, the biostimulator may be removed or repositioned from the fixation site with minimal damage to tissue at the fixation site. Disengagement of one or more of the sutures may also be controlled by positioning the sutures such that bending of the sutures during counter rotation is obstructed by the primary fixation feature/helical screw.

Other biostimulators in accordance with this disclosure include various non-suture features/mechanisms for providing anti-unscrewing functionality. In one implementation, an elastomeric or otherwise flexible sleeve is disposed on a primary helix of the leadless pacemaker. The flexible sleeve can include an apex, e.g., barb tips of a set of barbs that extend in a direction opposite that of the primary helix or similar primary fixation feature, such that the apex engages adjacent tissue when the leadless pacemaker is unscrewed. In other words, the sleeve functions as a secondary fixation feature that resists rotation of the leadless pacemaker in a direction opposite that of the primary fixation feature. The resistance provided by the apex generally resists the gradual unscrewing caused by regular movement of the patient and/or the patient's heart, however, the sleeve, e.g., one or more of the barbs, is sufficiently flexible such that the sleeve may be deformed and/or made to disengage cardiac tissue if a sufficient counter-torque is applied. By doing so, the leadless pacemaker may be removed and/or repositioned.

The present disclosure is also directed to lateral fixation features (a type of secondary fixation feature) that similarly provide anti-unscrewing functionality. The lateral fixation features are formed from a thin sheet and extend laterally from a location adjacent a distal end of the leadless pacemaker. In certain implementations, the lateral fixation features are used in conjunction with a primary fixation helix or similar primary fixation feature. In such cases, the lateral fixation features function as secondary fixation features that extend in a direction opposite the primary fixation feature and resist counter-rotation of the leadless pacemaker. In other implementations, the lateral fixation features incorporate both primary and secondary fixation features and, as a result, may obviate the need for a primary fixation helix. For example, the lateral fixation features may each include a body extending in a first direction and that acts as the primary fixation feature for implanting the leadless pacemaker into cardiac tissue. One or more barbs, prongs, spurs, or similar anti-rotation structures may be coupled to or integrally formed with the body and may extend from the body in a second direction opposite the first direction. As a result, the anti-rotation structure functions as a secondary fixation feature that resists unscrewing of the leadless pacemaker.

A. Leadless Biostimulator Including an Anti-Unscrewing Sleeve

As previously discussed, leadless biostimulators, such as leadless pacemakers, may include a fixation feature to ensure that the sensing/pacing electrode of the leadless biostimulator maintains good electrical contact with the cardiac tissue within which the leadless biostimulator is implanted. In certain leadless biostimulators, such fixation mechanisms may include a helical screw. In addition to the helix a secondary fixation or "anti-rotation" mechanism, such as angled sutures, may be implemented to prevent the leadless biostimulator from rotating opposite the screwing direction of the helix and potentially counter-rotating out of implantation.

Fixation of leadless biostimulators within certain areas of the heart may present particular challenges. For example, fixation in the right atrium is made difficult due to the shape of the right atrium. More specifically, the shape of the right atrium generally precludes the use of laterally extending secondary fixation features. As a result, secondary fixation features for use in such applications may generally extend in a substantially distal direction. However, in leadless biostimulators such as the leadless biostimulator 200 of FIG. 2, in which distally extending sutures are implemented as secondary fixation features, such sutures may be undesirably close to the pacing/sensing electrode. As a result of such proximity, the sutures may cause the formation of scar tissue adjacent to the electrode resulting in an increased pacing threshold. In light of this issue, it would be advantageous to have alternative secondary fixation features that are substantially displaced relative to the electrode and, as a result, minimize the formation of scar tissue adjacent to the electrode.

In addition to issues related to scar tissue formation, the relatively small scale of leadless biostimulators significantly limit the types of processes available for manufacturing and assembling leadless biostimulators. For example, many features of leadless biostimulators are on the order of 0.001 inches to 0.010 inches and, as a result, are unable to hold tolerances when using conventional machining or molding processes. Other manufacturing processes more suited to the scale of leadless biostimulator components can be prohibitively costly.

In one implementation of the present disclosure, a leadless biostimulator is provided that includes a primary fixation feature, such as a primary fixation helix. The primary fixation feature can be attached to a distal end of the leadless biostimulator for use in securing the leadless pacemaker to a wall of the heart. The leadless biostimulator further includes a secondary fixation feature in the form of a thin-wall sleeve coupled to the primary fixation feature adjacent to or around the tip of the primary fixation feature. The secondary fixation feature may be formed by, among other things, extrusion, casting, or coating and may be formed in situ on the primary fixation feature. The secondary fixation feature may be formed to include a barb or similar counter-rotation feature that is configured to resist counter rotation of the leadless biostimulator after implantation. More specifically, the primary fixation feature is generally adapted to engage the wall of the heart by being rotated in a first direction (e.g., a screwing direction). The secondary fixation feature is shaped and disposed on the primary fixation feature such that, once implanted, the counter-rotation feature resists rotation of the leadless biostimulator in a second direction opposite the first direction, (e.g., an unscrewing direction) by engaging the wall of the heart.

The secondary fixation feature is generally placed adjacent to the tip of the primary fixation feature such that the secondary fixation is optimally placed to prevent rotation of the leadless biostimulator in the second direction. The secondary fixation feature is also generally disposed at or near the distal extent of the primary fixation feature such that the secondary feature does not interfere with a stimulation electrode of the leadless biostimulator.

Implementations of the present disclosure solve the issues related to the relatively small scale of leadless biostimulators by enabling the use of extrusion, casting, or coating processes to produce a very thin wall tube. The tube is then trimmed, die-cut, laser-cut, or otherwise processed to produce the final secondary fixation feature. By doing so, the secondary fixation feature may be manufactured in a cost-effective yet precise manner despite its small size.

In certain implementations, the geometric profile, wall thickness, material, and other aspects of the secondary fixation feature are chosen such that the secondary fixation feature resists counter-rotation of the leadless biostimulator up to a first predetermined torque. If a torque is applied that exceeds the first predetermined torque, the secondary fixation feature is adapted to bend, flex, or otherwise deform, backing against itself and allowing the leadless biostimulator to be unscrewed and subsequently removed or repositioned without severely damaging the tissue at the original implantation site. More particularly, the secondary fixation feature is configured such that, when implanted within the heart, a first torque in the unscrewing direction opposite the screwing direction causes the secondary fixation feature to engage the heart and provide a first resistance to rotation of the leadless biostimulator in the unscrewing direction. The secondary fixation feature is further configured, however, such that, when implanted within the heart, a second torque in the unscrewing direction greater than the first torque causes deformation of the secondary fixation feature to at least partially disengage the secondary fixation feature from the heart and provide a second resistance less than the first resistance to rotation of the leadless biostimulator in the unscrewing direction.

Figure 3:
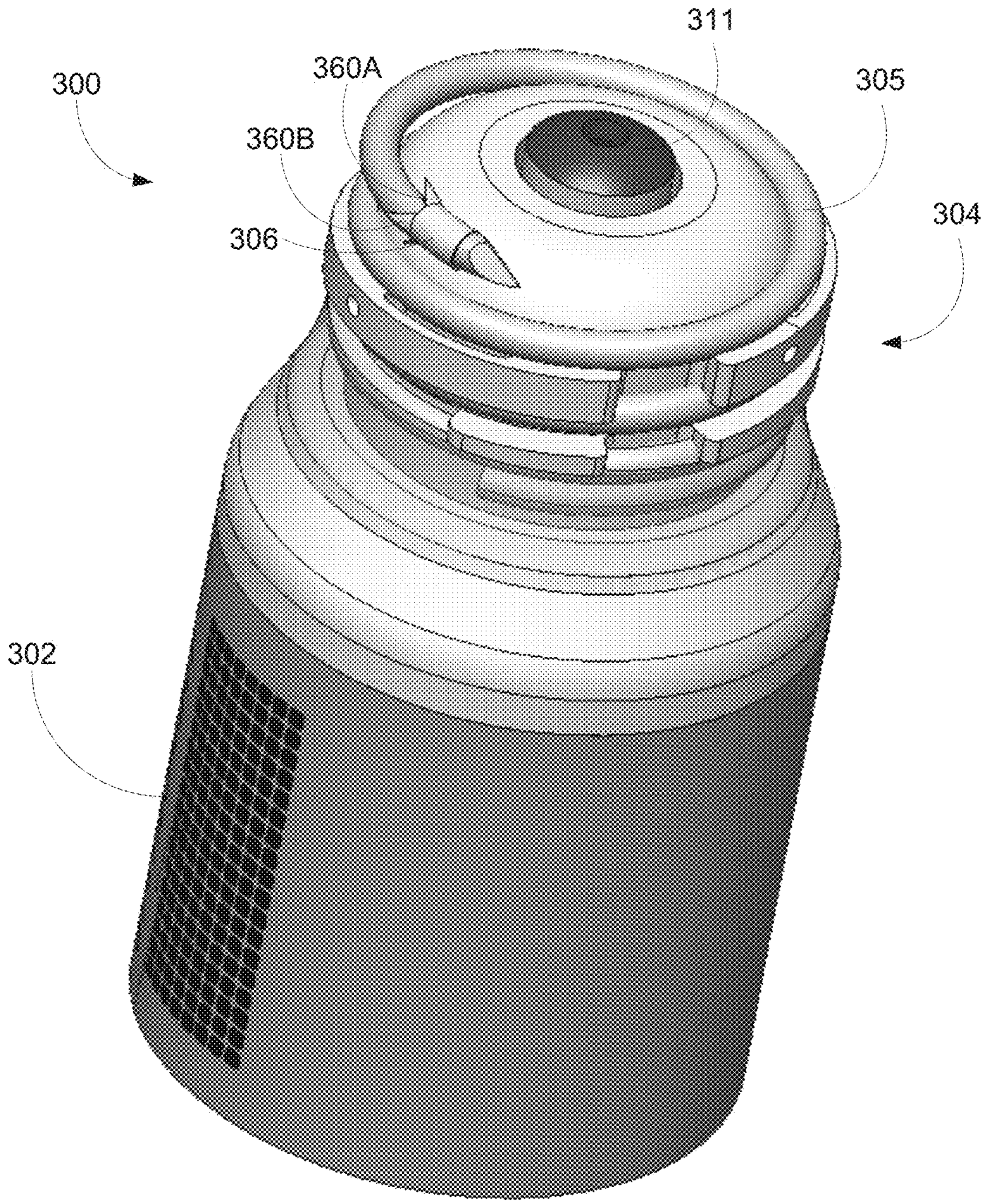
FIG. 3-4 are isometric views of a second biostimulator including a secondary fixation feature in the form of a sleeve, in accordance with an embodiment.
Figure 4:
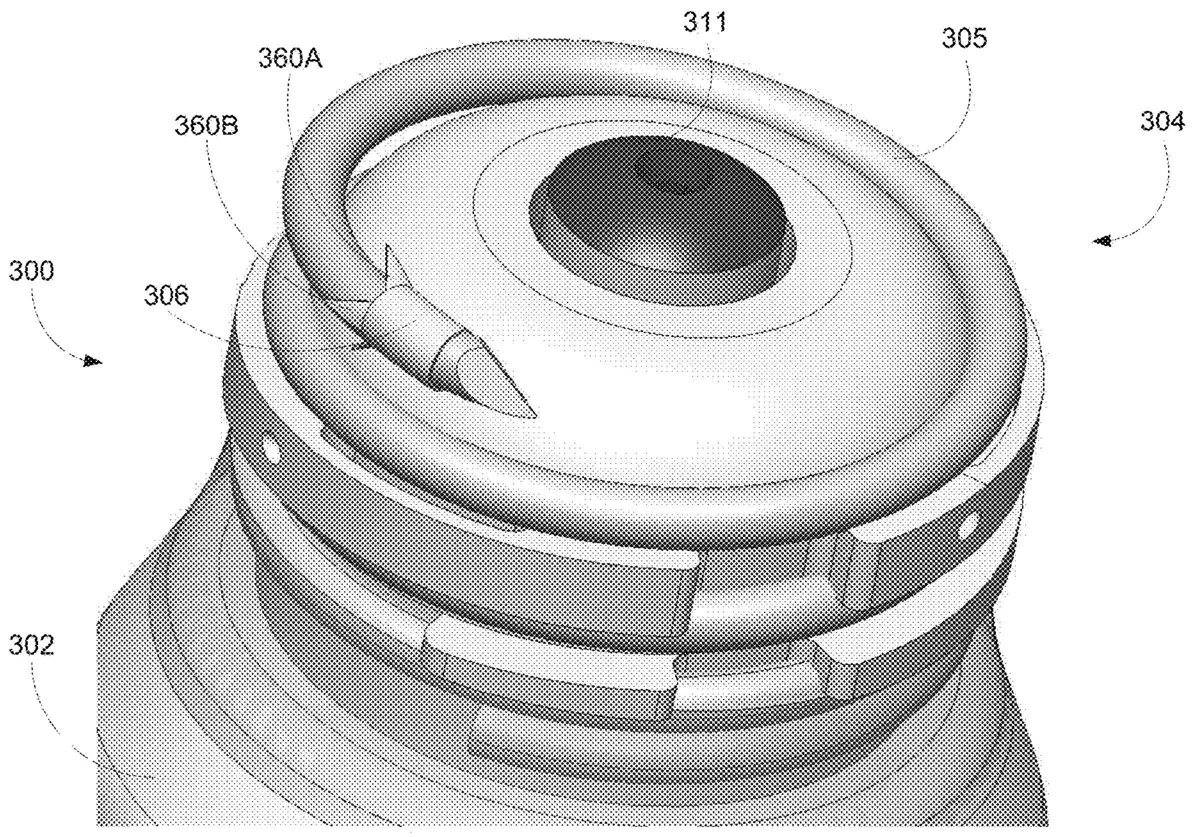

FIGS. 3 and 4 are isometric views of a biostimulator 300 in accordance with an embodiment. The biostimulator 300 includes a housing 302 and a header assembly 304 coupled thereto. The housing 302 may be sized to be implanted within a heart of a patient. Coupling of the housing 302 to the header assembly 304 may be accomplished in various ways including, without limitation, one or more of a biocompatible adhesive, a threaded connection, or ultrasonic welding.

The header assembly 304 generally includes a primary fixation feature 305 and a secondary fixation feature 306. The primary fixation feature 305 can be similar or identical to the primary fixation device 205 described above, e.g., the primary helix 205. Accordingly, when the header assembly 304 is mounted on the housing 302, the primary fixation feature 305 is coupled to the housing 302. Likewise, the secondary fixation feature 306 can be coupled to the primary fixation feature 305. For example, the secondary fixation feature 306 may be a separate component disposed or mounted on the primary fixation feature 305. Alternatively, the secondary fixation feature 306 can be integrally formed with and disposed on the primary fixation feature 305. In general, the secondary fixation feature 306 functions as an anti-unscrewing feature that resists unscrewing of the biostimulator 300 after implantation.

In the specific example of FIGS. 3 and 4, the primary fixation device 305 is a primary helix 305 pointing in a first direction, e.g., spiraling in a clockwise direction. The secondary fixation feature 306 includes a sleeve 306 disposed or mounted near a distal extent of the primary helix 305. For example, the sleeve 306 can be disposed about a helical wire of the primary fixation device 305 by sliding the sleeve 306 onto the primary helix 305. The sleeve 306 can have one or more anti-rotation features facing a second direction opposite the first direction, e.g., in an anticlockwise direction.

The primary helix 305 may be substantially formed of any suitable biocompatible material including, without limitation, one or more of stainless steel, nickel-titanium alloys (such as Nitinol), nickel-chromium allows (such as Incoloy®), titanium, or multiphase nickel alloys (such as MP35N®). In certain implementations, the substrate material of the primary helix 305 may also be conductive such that the primary helix 305 may be used as an electrode for sensing and/or pacing of cardiac tissue.

The primary helix 305 is preferably sized to couple the biostimulator 300 to cardiac tissue while minimizing damage to the cardiac tissue. In certain implementations, for example, the primary helix 305 extends from and including 0.25 turns to and including 3 turns from the helix mount 206, has a wire diameter from and including 0.003 inches to and including 0.03 inches, has a pitch diameter from and including 0.06 inches to and including 0.3 inches, and has a pitch from and including 0.01 inches to and including 0.05 inches. While the implementations illustrated herein include a single primary helix 305, other implementations of the present disclosure may include multiple fixation helices, each extending in the same direction and each adapted to engage cardiac tissue in response to rotation of the biostimulator 300. Such multi-helix implementations may include biostimulators with multifilar helices in which multiple wires are conjoined, e.g., jointly wound, or biostimulators including multiple offset helices. In implementations in which multiple helices are implemented, any or all of the helices may include a respective secondary fixation feature 306 to resist counter-rotation.

As illustrated in FIGS. 3-4, the sleeve 306 is generally disposed at or near the distal end of the primary fixation feature 305. Coupling of the sleeve 306 to the primary fixation feature 305 may be achieved in various ways. In certain implementations, the sleeve 306 is directly molded or otherwise formed on the primary fixation feature 305. For example, the sleeve 306 may be overmolded, cast, or extruded directly onto the primary fixation feature 305. In other implementations, the sleeve 306 may be separately formed and then subsequently disposed on the primary fixation feature 305. For example, the separate sleeve 306 can be mounted on and attached to, e.g., adhered to, the primary fixation feature 305. In such implementations, the sleeve 306 may be coupled to the primary fixation feature 305, among other ways, by a biocompatible adhesive or by heat-shrinking the sleeve 306 onto the primary fixation feature 305 (when sleeve 306 is fabricated from a heat-shrink material). To facilitate coupling between the primary fixation feature 305 and the sleeve 306, one or both of a surface of the primary fixation feature 305 and an inner surface of the sleeve 306 may be textured or otherwise roughened to improve adhesion.

As illustrated in FIG. 3, the sleeve 306 may be disposed at or near a tip of the primary fixation feature 305. In other implementations, the sleeve 306 may be disposed at other locations along the primary fixation feature 305. For example, in certain implementations the sleeve 306 may be disposed or mounted on the first quarter, first half, first three-quarter, or first full distal turn of the primary fixation feature 305.

As described below in the context of FIGS. 18A-18B, implantation of the leadless biostimulator 300 is generally accomplished using a delivery catheter or similar delivery catheter that may be used to guide the leadless biostimulator 300 to an implantation location adjacent a wall of a chamber of the heart. Once located, the delivery catheter may be rotated in a screwing direction, thereby causing the primary fixation feature 305 to engage the wall of the heart. More particularly, rotation of the primary fixation feature 305 in the screwing direction affixes the housing 302 to the heart of the patient. As the leadless biostimulator 300 is further rotated, an electrode 311 of the leadless biostimulator 300 is brought into contact with the wall of the heart such that the leadless biostimulator 300 can deliver electrical impulses to the adjacent heart tissue.

As the primary fixation feature 305 is implanted into the wall of the heart, the secondary fixation feature 306 is brought into proximity with the wall of the heart as well. More specifically, the secondary fixation feature 306 is disposed adjacent to the wall of the heart such that the secondary fixation feature is able to resist counter-rotation of the implanted biostimulator 300. Such counter-rotation may be the result of, among other things, movement of the patient or beating of the heart. As described below in more detail in the context of FIGS. 5A-5D, the sleeve 306 may include barbs, such as barbs 360A-360B, or similar anti-rotation features that extend in a direction substantially opposite the screwing direction of the primary fixation feature 305. Accordingly, as counter-torque is applied to the biostimulator 300, the anti-rotation feature engages the wall of the heart to resist counter rotation of the biostimulator 300.

In certain implementations, one or more of the secondary fixation features (also referred to herein as anti-rotation features) may be adapted to resist counter torque up to a predetermined limit but to disengage the wall of the heart when the predetermined limit is exceeded. For example, the barbs 360A-360B may be formed of a flexible material capable of resisting a first counter torque but if a second counter torque is applied that is greater than the first counter torque, the barbs 360A-360B may deflect, bend, compress, buckle, or otherwise deform such that the barbs 360A-360B are no longer pointed in a direction substantially opposite the primary fixation feature 305. When so deformed, the biostimulator 300 may be counter rotated to disengage the primary fixation feature 305, thereby enabling removal and/or repositioning of the biostimulator 300. In certain implementations, the first counter torque may generally correspond to the anticipated counter torque that may be experienced during regular patient activity plus a predetermined safety factor. For example, the first counter torque may be up to and including 0.5 ounce-inches (oz-in). In certain implementations, the second counter torque may generally correspond to a predetermined force required to be applied by a retrieval catheter or similar retrieval system that may be used to retrieve/remove the biostimulator 300 following implantation. In such implementations, the second counter torque may be from and including 0.5 oz-in to and including 2.0 oz-in, for example.

The first and second counter torque values above are provided by way of example. In an embodiment, the second counter torque is higher than the first counter torque, and may be higher by a scale factor. The scale factor can be a multiplier that provides more resistance to disengagement under torque. For example, the second counter torque may be at least 5 times the first counter torque, e.g., the second counter torque may be equal to the first counter torque times the scale factor of 10.

Figure 5A:
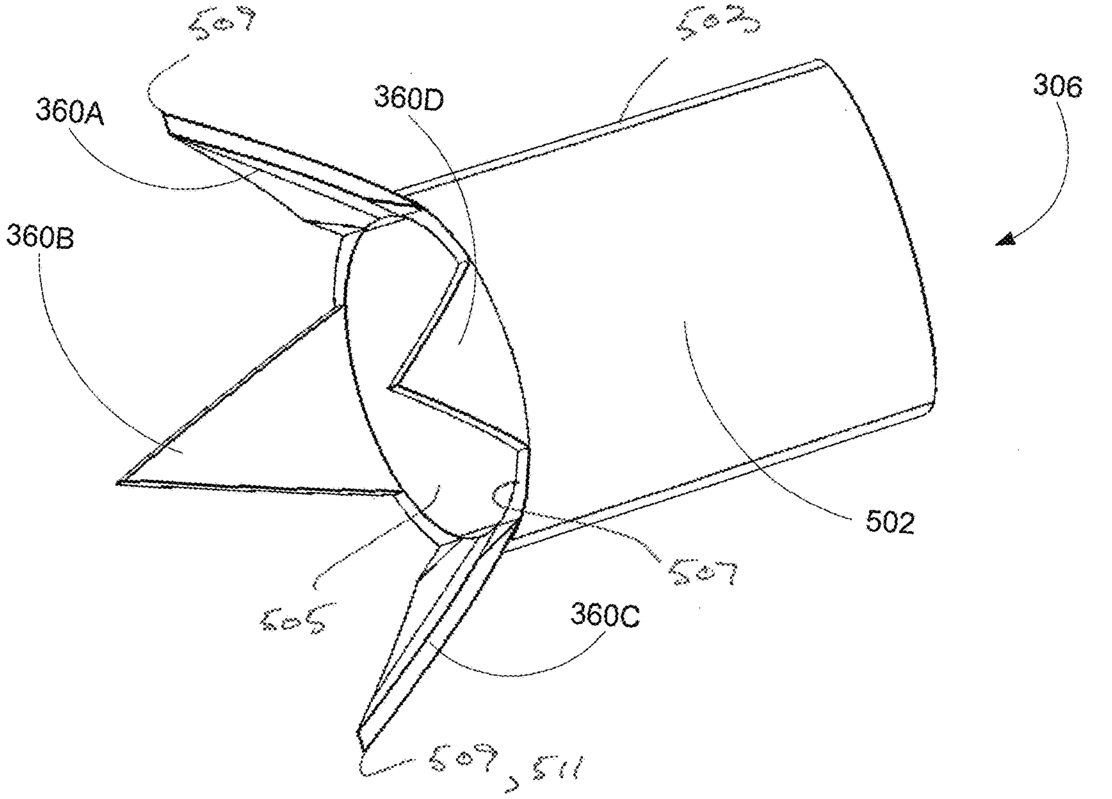
FIGS. 5A-5B are isometric and side elevation views, respectively, of the sleeve of FIGS. 3 and 4, in accordance with an embodiment.
Figure 5B:
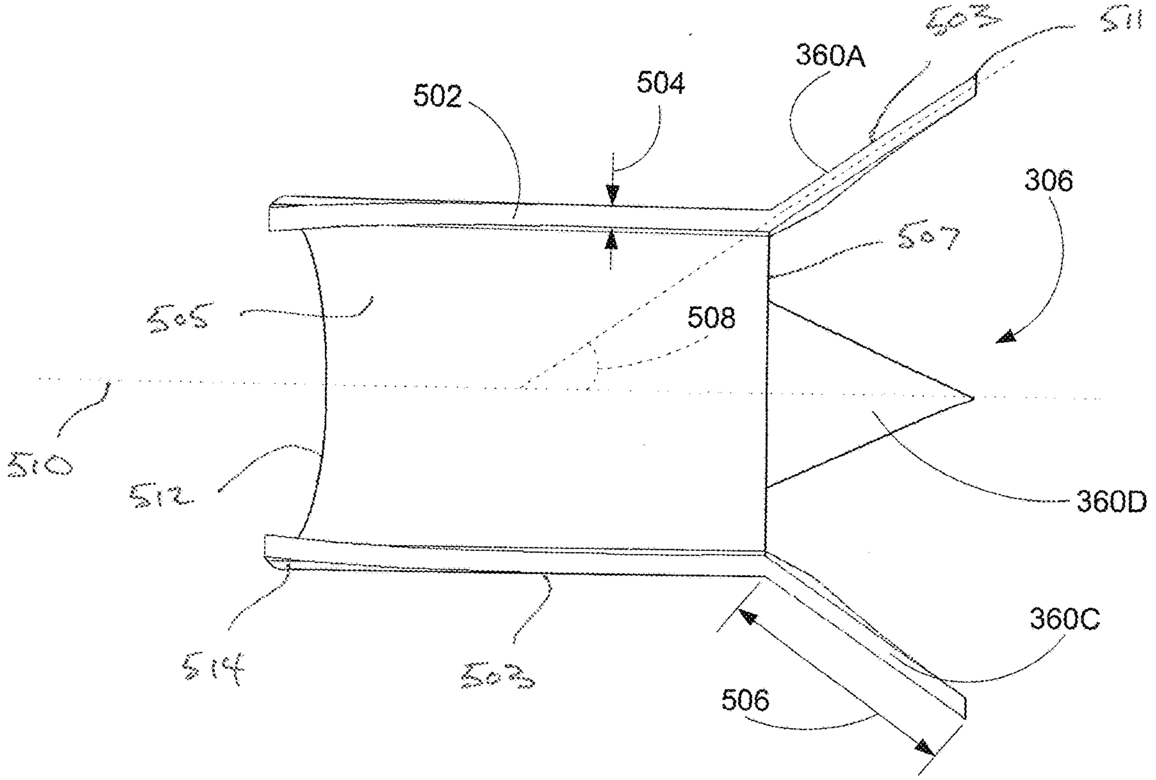

FIGS. 5A-5B are an isometric view and a cross-sectional side view of the sleeve 306 of FIGS. 3-4 and are intended to illustrate aspects of the sleeve 306 in further detail.

As illustrated in FIGS. 5A-5B, the sleeve 306 generally includes a body 502 from which one or more anti-rotation features extend. The body 502 can be a tubular body, e.g., a body having a cylindrical outer surface 503 and a lumen 505 extending longitudinally through the body. An annular cross-section of the body 503 can be disposed about a conforming cylindrical outer surface of the primary helix 305.

One or more anti-rotation features can extend from the body 503 of the sleeve 306. For example, a barb 360 can extend at an angle from a first end 507 of the body 503. The barb 360 can be one of several flexible barbs 360A-360D, each of which can include respective barb tips 509. The outer surface 503 can extend over the barb(s) from the first end 507 to the barb tips 509. Given that the barbs 360A-360D can extend at an angle, e.g., in the unscrewing direction, from the first end 507, the outer surface 503 can similarly taper radially outward to the barb tip 509. In an embodiment, the barb tip 509 is a radially outward limit of the sleeve 306, and accordingly, the barb tips 509 are at an apex 511 of the sleeve 306. More particularly, the sleeve 306 include outer surface 503 tapering radially outward to the apex 511 at a radially outward-most location.

The barbs 360A-360D can be distributed about the circumference of the tubular body 502. For example, four barbs may be distributed about the circumference. In other implementations, other anti-rotation features may be implemented. For example, and without limitation, such anti-rotation features may include barbs having shapes that are other than triangular. By way of example, the anti-rotation features may be elongated cylinders, e.g., include sutures or threads extending from the body. Moreover, the number of anti-rotation features may also vary in other implementations. Although illustrated as including four anti-rotation features 360A-360D in FIGS. 5A-5B, in other implementations, other numbers of anti-rotation features may be used. For example, and without limitation, implementations may include any of one, two, three, or any number greater than four barbs.

As previously discussed, the anti-rotation features 360A-360D may be flexible such that counter-rotation of the leadless biostimulator 300 after implantation is resisted. When sufficient counter-torque is applied, however, the anti-rotation features 360A-360D may flex or otherwise deform, thereby enabling disengagement of the leadless biostimulator 300. To achieve such flexibility, the sleeve 306 may be formed from a flexible plastic, such as polyimide. For example, the sleeve 306 may be formed by extruding or otherwise manufacturing a polyimide tube that is then cut (such as by die cutting, waterjet cutting, laser cutting, or a similar cutting method) or similarly processed to form the anti-rotation features 360A-360D.

Materials for the sleeve 306 may also be selected based on particular properties or characteristics. For example, in certain implementations, the sleeve 306 may be formed from a flexible material, e.g., polyimide as described above, or another flexible biocompatible material including, without limitation, one or more of polyester, polyethylene, polypropylene, polyurethane, polyether ether ketone (PEEK), or polyvinylidene fluoride. Sleeve 306 may be formed from one or more flexible materials, and the term "flexible" may be (although not necessarily) defined as having a Young's modulus from and including 0.5 GPa to and including 10 GPa. Such material characteristics provide for adequate flexibility to allow the sleeve 306 to yield to a predetermined counter-torque, as described above. Material selection for the sleeve 306 may alternatively be based on material toughness which may be associated with specific tensile and compression strengths of the material.

In an embodiment, one or more portions of the secondary fixation feature, e.g., the sleeve 306, may be formed from a bioabsorbable and/or bioresorbable material. Examples of suitable bioresorbable polymers include polyglycolide (PGA), polylactide (PLA), polycaprolactone (PCL), polydioxanone (PDO), polytrimethylene carbonate (TMC), and co-polymers thereof. Examples of suitable bioresorbable metals include magnesium alloys, iron alloys, zinc alloys, and combinations thereof. The bioresorbable material may be a magnesium-rare earth alloy with dysprosium as the main alloying element. For example, the bioresorbable material may be RESOLOY®. The bioabsorbable secondary fixation feature may exhibit surface erosion and/or bulk degradation during absorption into the heart following implantation.

A bioabsorbable secondary fixation feature may be tuned to absorb into the target tissue over a predetermined time range. The absorption profile can be tuned by the composition of the bioresorbable material, e.g., the monomers selected, the ratio of monomers in a co-polymer, the polymer chain length, and/or by a geometry of the secondary fixation feature. For example, in the embodiment of FIGS. 5C-5D, a shape and/or cross-sectional area, such as the tapers at either ends of the sleeve 360, can be selected to control a rate of absorption. The geometry can cause the sleeve to absorb over a predetermined period of time. The time range may be selected to allow for complete absorption to occur after tissue has endothelialized around the secondary fixation feature. By choosing such an absorption profile, the tissue fibers can form a matrix around the primary fixation feature to secure the leadless pacemaker and prevent backout after the secondary fixation feature is fully resorbed.

The sleeve 306 may, in certain implementations, be formed from multiple materials. For example, the tubular body 502 and barbs 360A-360D may be formed from different materials, with the tubular body 502 being relatively more rigid that the barbs 360A-360D.

Various aspects of the sleeve 306 may conform to predetermined dimensional ranges. For example, the tubular body 502 may have a thickness 504 from and including 0.001 inches to and including 0.010 inches and each of the triangular barbs 360A-360D may have a length (such as barb length 506 of barb 360C) from and including 0.005 inches to and including 0.200 inches. Each of the barbs 360A-360D may also be biased to extend at an angle 508 relative to a longitudinal axis 510 of the sleeve 306, the angle 508 being up to and including 90 degrees. As described above, the body 502 can include a first end 507, and the outer surface 503 can taper from the first end 507 to the apex 511 at the barb tip(s).

As illustrated in FIG. 5B, the body 502 may also include a second end 512 opposite the anti-rotation features 360A-360D. More particularly, the second end 512 can be on an opposite end of the body 502 from the first end 507. In an embodiment, the second end 512 include a taper 514. For example, the taper 514 can be a portion of the body 502 that narrows or tapers toward the longitudinal axis 510 of the sleeve 306. Alternatively, the second end 512 may have an external edge that is radiused, filleted, or similarly profiled. The outer surface 503 can have an outer dimension that decreases in the screwing direction over the taper 514. Such a feature on the second end 512 may generally prevent the second end 512 of the sleeve from catching or otherwise engaging adjacent heart tissue during implantation of the leadless biostimulator 300 because the taper 514 can wedge along, rather than catch on, the tissue during implantation. Accordingly, the taper 514 can reduce the likelihood of unintentional damage during implantation.

Figure 5C:
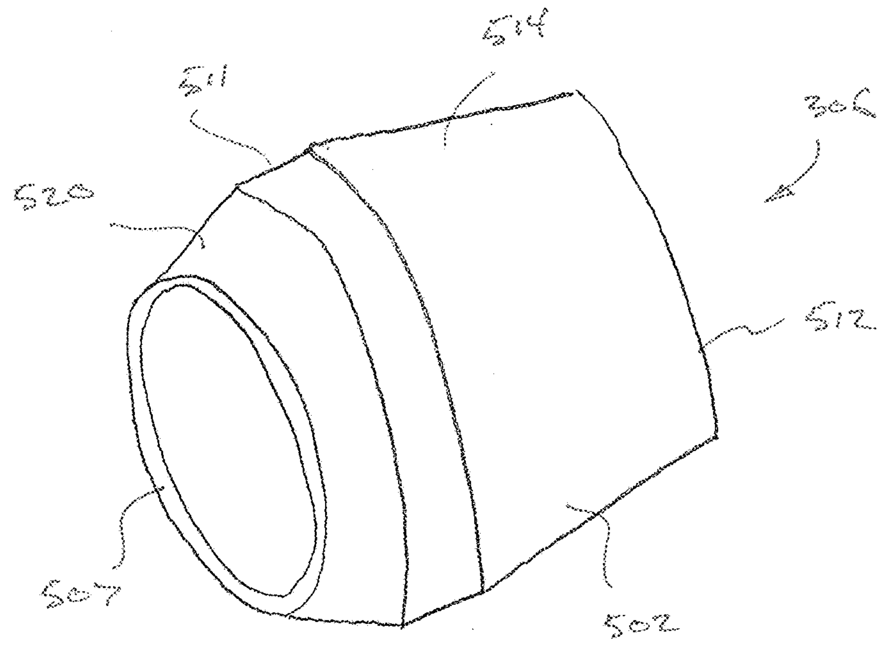
FIGS. 5C-5D are isometric and side elevation views, respectively, of an alternative sleeve, in accordance with an embodiment.
Figure 5D:
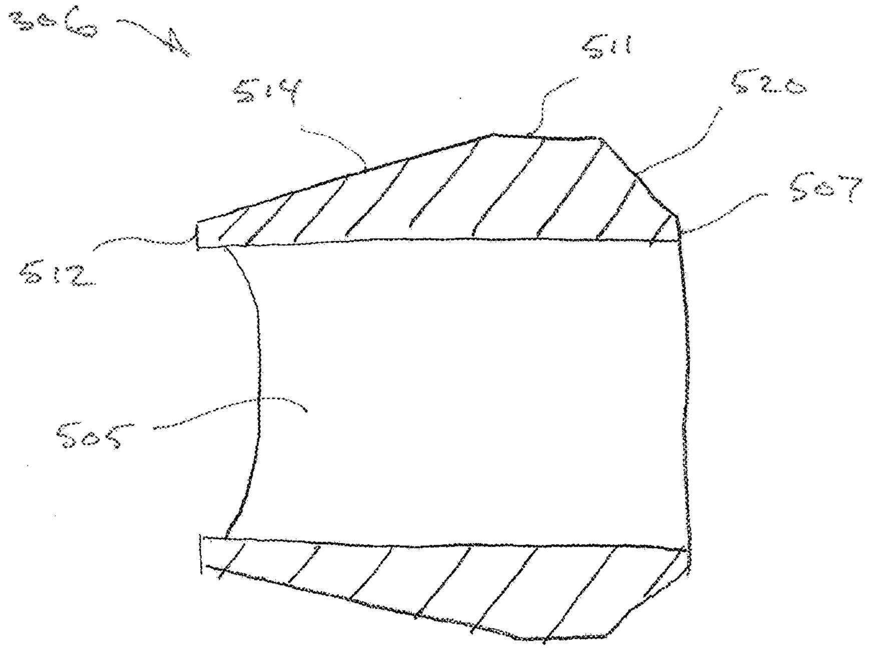

FIGS. 5C-5D are isometric and side elevation views, respectively, of the sleeve, in accordance with an embodiment. The sleeve 306 may have an alternative anti-rotation feature, as compared to the barbs 360A-360D. In any embodiments, the sleeve 306 can provide resistance to movement in the unscrewing direction, and the anti-rotation features can be shaped to facilitate such a function. The anti-rotation feature may, however, be barbless.

In an embodiment, a barbless sleeve 306 may be asymmetrically shaped to preferentially move in the screwing direction. More particularly, the sleeve 306 may move more easily in the screwing direction than in the unscrewing direction. The sleeve 306 can include a ferrule having the body 502. More particularly, the ferrule can include an annular body 502 extending from the first end 507 to the second end 512. The annular body 502 may include one or more tapers extending from respective ends to the apex 511 at a radially outward-most location. For example, a first taper 520 can taper radially outward in a first direction, e.g., the screwing direction, and a second taper 514 can taper radially outward in a second direction opposite to the first direction, e.g., the unscrewing direction. The tapers 514, 520 can meet at a ridge extending along the apex 514, or the apex

511 can be a cylindrical portion of the body 502 separating the outermost points on the tapers 514, 520 as shown. The apex 511 can be longitudinally between end 507, 512.

The length and/or angle of each of the tapers can affect an amount of torque required to move the ferrule against tissue. For example, the steeper the taper, the more torque that is required to wedge the taper along tissue when the taper is in contact with the tissue. In an embodiment, the first taper 520 faces the unscrewing direction, and thus, the first taper 520 can have a higher angle relative to the longitudinal axis of the sleeve 306 as compared to the second taper 514. Accordingly, more torque is required to move the ferrule in the unscrewing direction than in the screwing direction. Movement in the screwing direction is relatively easier because the second taper 514 has a smaller angle relative to the longitudinal axis, and thus, wedges more gradually along the tissue. Similar to the taper 514 of FIG. 5A, the second taper 514 of FIG. 5C facilitates movement in the screwing direction. Likewise, similar to the barbs 360A-360D of FIG. 5A, the first taper 520 of FIG. 5C resists movement in the unscrewing direction.

Referring to FIG. 5D, it can be seen that in cross-section there may be no sharp edges on the sleeve 306 that includes the ferrule configuration. A lack of sharp edges, such as the barb tips 509, can reduce the likelihood of causing tissue trauma when the primary fixation feature 305 is unscrewed. The tapers of the ferrule, however, provide sufficient resistance to unscrewing that the sleeve 306 prevents disengagement of the primary fixation feature 305 from the heart. Accordingly, barbless secondary fixation features 306 can achieve resistance to unscrewing while reducing the likelihood of tissue trauma.

A method of manufacturing the leadless biostimulator 300 can include forming the secondary fixation feature 306, which includes the sleeve. Forming the sleeve 306 can include one or more operations. For example, forming the sleeve 306 can include forming the tubular body 502, and cutting the tubular body 502 to form one or more barbs 360. Alternatively, forming the sleeve 306 can include a single operation, e.g., fabricating the ferrule from a bioabsorbable material in a machining or molding operation. The method can include disposing the secondary fixation feature 306 on a distal portion of the primary fixation feature 305. For example, the secondary fixation feature 306 can be mounted on the primary fixation feature 305, or the secondary fixation feature 306 can be directly formed onto the primary fixation feature 305.

B. Leadless Biostimulator Having a Planar Fixation Feature Including Primary and Secondary Fixation Features As previously discussed, various issues may arise when fixing a leadless biostimulator within the heart and, in particular, when requiring both a primary fixation feature for securing the biostimulator to the wall of the heart during implantation and a secondary fixation feature to reduce or prevent the leadless biostimulator from unscrewing or otherwise detaching once implanted. Among other issues, the placement of such fixation features relative to an electrode of the biostimulator may be problematic in that if there is insufficient spacing, the fixation features may cause the formation of scar tissue adjacent to the electrode, thereby increasing pacing and sensing thresholds. Another issue arises from the general scale of leadless biostimulators and the ineffectiveness of conventional manufacturing techniques in maintaining the required tolerances for such fixation features.

To address these issues, among others, another implementation of a leadless biostimulator is provided in which the primary fixation helix of the previously discussed examples is omitted. Instead, each of primary and secondary fixation are achieved using a planar fixation feature having laterally extending arms. In certain implementations, the planar fixation feature is disposed proximal to an electrode of the biostimulator, thereby reducing the likelihood that the planar fixation feature will form interfering scar tissue. The planar fixation feature may also be formed from converted or extruded thin-wall sheeting, thereby improving overall manufacturability of the planar fixation feature.

As discussed below in more detail, the planar fixation feature may include a body from which a series of arms extend. Each of the arms extends in the same direction such that by rotating the leadless biostimulator in the direction of the arms, pointed tips of the arms may be inserted into the wall of the heart, thereby implanting the leadless biostimulator. Each of the arms further includes a respective secondary fixation feature adjacent to the pointed tip that extends opposite the direction of the arm. Each secondary fixation feature may, for example, be in the form of a hook, a barb, or a similar protrusion. By extending in a direction opposite the arm, the secondary fixation features resist counter-rotation of the leadless biostimulator once implanted.

The geometric profile and the wall thickness of the sheeting from which the planar fixation feature is formed, is chosen such that the arm can easily pierce the endocardium and engage with tissue securely with a reasonable amount of forward pressure and torsion. However, the sheeting is also chosen such that the counter-rotational resistance provided by the secondary fixation feature may be overcome should a change in placement or removal of the biostimulator be required. More specifically, the sheeting is chosen such that by applying an overload torque (e.g., a torque that generally exceeds that which would be experienced by the biostimulator during normal cardiac activity) in the counter-rotational direction, the secondary fixation feature may be made to bend back on itself, give, or otherwise deform allowing the biostimulator to be unscrewed without severely damaging the tissue adjacent to the initial implantation site.

Implementations of the present disclosure including planar fixation features take advantage of film converting processes or similar manufacturing techniques to tightly control a first dimension (i.e., the thickness) of the fixation feature. For example, depending on the particular material used, such manufacturing techniques can achieve consistent thicknesses in the range of 0.001 inches to 0.02 inches with significantly tighter tolerances than comparable machining or molding processes. The planar fixation feature, and more specifically the arms and bars, may then be trimmed or cut from the formed sheet, such as by using a blade, a die, a waterjet, or laser.

Placing the secondary fixation features (e.g., the barbs) immediately adjacent to the primary fixation features (e.g., the tips of the arms), can optimally achieve both primary and secondary fixation because the counter-rotational resistance provided by the secondary fixation features is directed in the immediate vicinity of the primary fixation location. In other words, since the secondary fixation barbs are integrated with the arms, secondary fixation is guaranteed once the arms are engaged with tissue.

As illustrated by the implementations described herein, the planar fixation feature may include multiple, integrated arms, each of which includes a corresponding secondary fixation feature. This redundant design enables for more reliable engagement of the biostimulator to the wall of the heart as there are more chances for tissue engagement and only one engagement is generally needed for adequate fixation of the biostimulator. Including multiple points of engagement also compensates for greater variance in tissue morphology. By including multiple fixation points, the amount of rotation required to engage the wall of the heart is also generally reduced, leading to a simpler delivery experience. Moreover, by integrating primary and secondary fixation features into one formed feature, the overall fixation design is greatly simplified while still meeting design requirements. Among other benefits, the simplified design increases manufacturing efficiency, decreases part costs, provides an improved fixation delivery experience for the end user, reduces the potential damage to tissue (thus improving pacing thresholds), and generally provides a more reliable fixation function.

Figure 6:
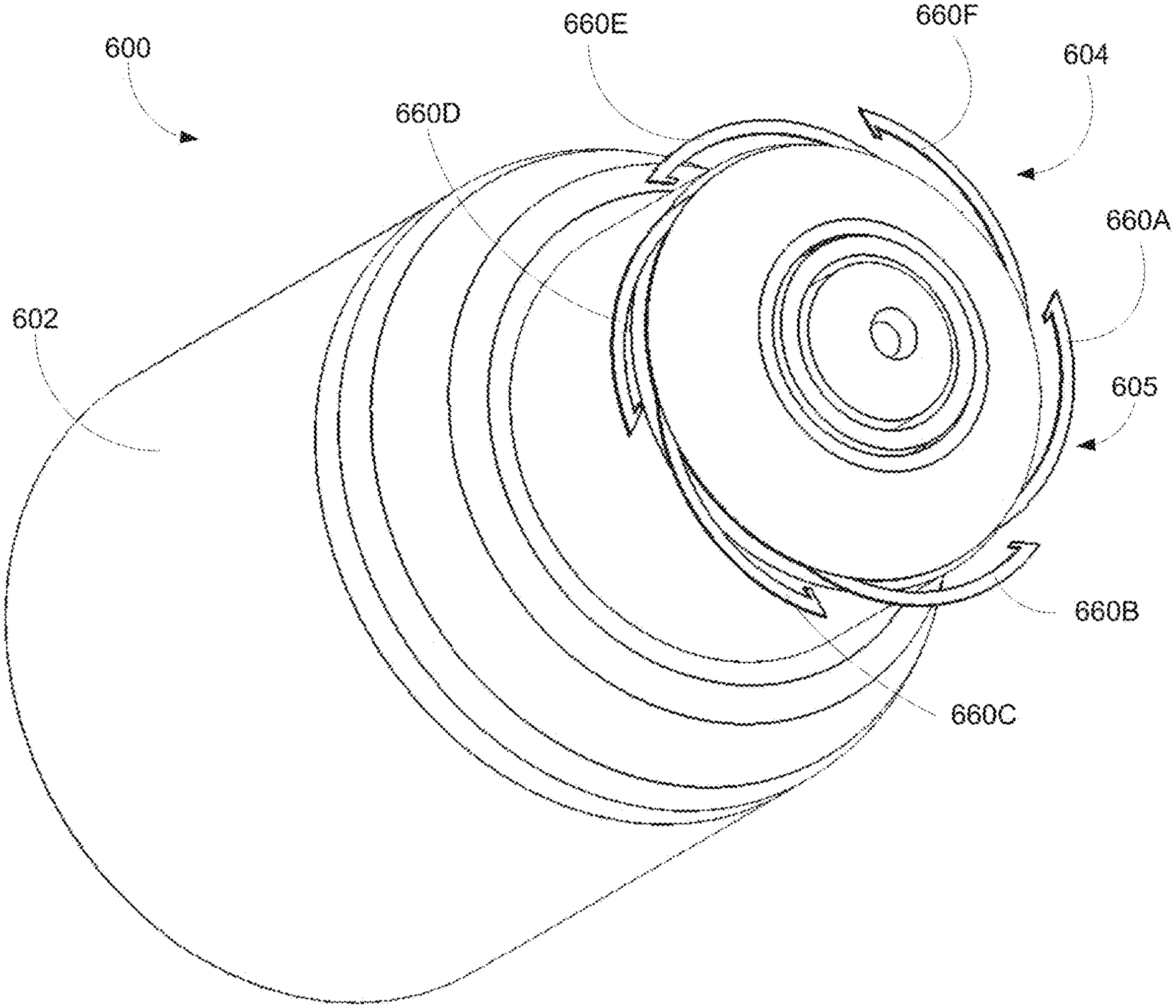
FIGS. 6-7 are isometric views of a third biostimulator including a planar fixation feature, in accordance with an embodiment.
Figure 7:
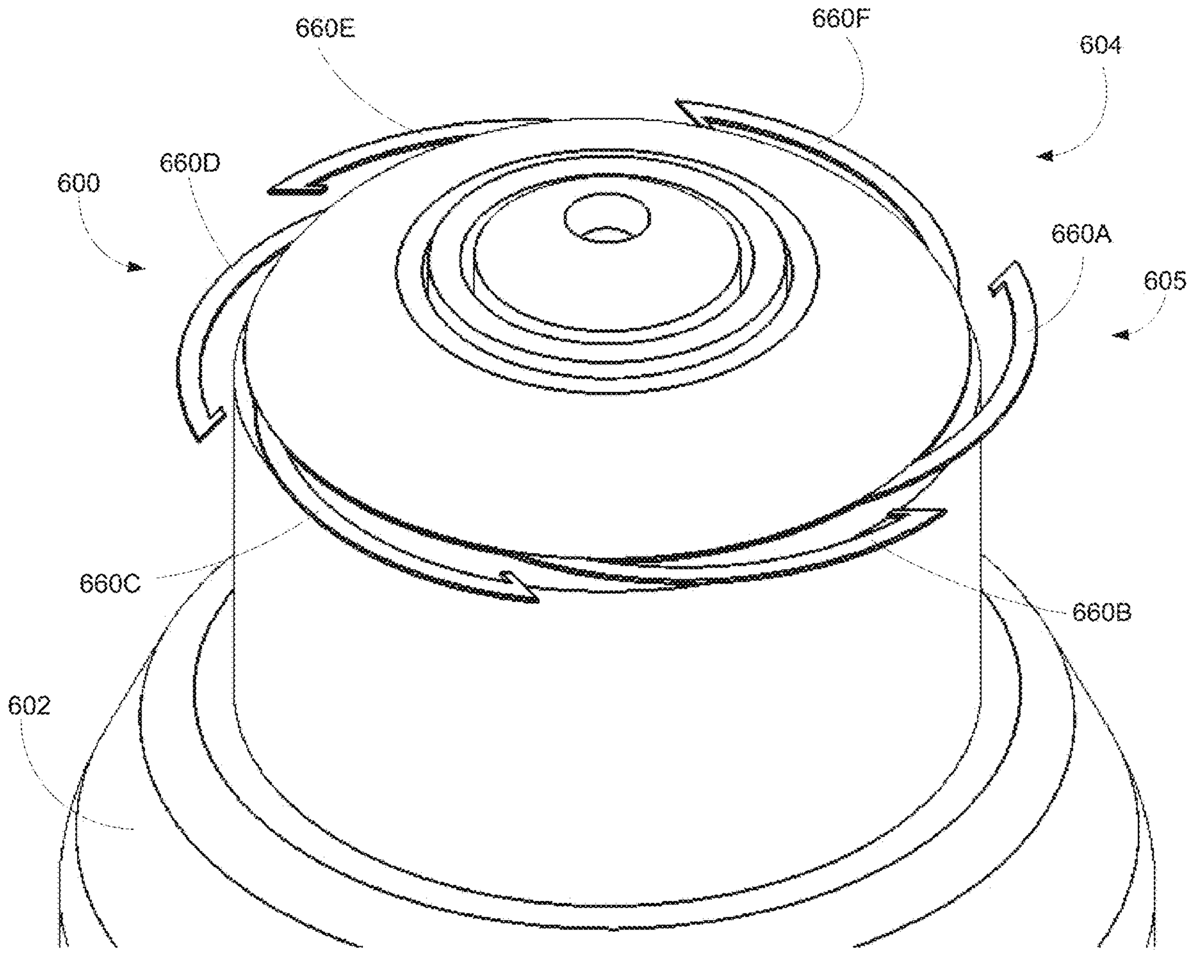

FIGS. 6 and 7 are isometric views of a biostimulator 600 in accordance with the present disclosure. The biostimulator 600 includes a housing 602 and a header assembly 604 coupled thereto. Coupling of the housing 602 to the header assembly 604 may be accomplished in various ways including, without limitation, one or more of a biocompatible adhesive, a threaded connection, or ultrasonic welding.

The header assembly 604 includes a planar fixation feature 605 extending laterally from the header assembly 604. The planar fixation feature 605 includes several arms 660A-660F for fixation of the leadless biostimulator 600 to a wall of the heart. More specifically, the arms 660A-660F provide both primary fixation functionality by enabling implantation of the leadless biostimulator 600 into the wall of the heart and secondary fixation functionality by resisting counter-rotation of the leadless biostimulator 600 following implantation. To do so, each of the arms 660A-660F extends in a first or screwing direction, terminating in a sharpened point 662A-662F (indicated in FIGS. 9A-9B). Accordingly, when the biostimulator 600 is brought into contact with a wall of the heart and rotated in the first direction, the arms 660A-660F engage and implant into the wall of the heart.

Each of the arms 660A-660F further includes a barb 664A-664F (indicated in FIGS. 9A-9B) or similar anti-rotation feature extending in a second or unscrewing direction opposite the screwing direction. Accordingly, once implanted, the barbs 664A-664F provide resistance to counter-torques that may arise from movement of the patient or cardiac activity and that may otherwise cause loosening and/or disengagement of the leadless biostimulator 600 from the wall of the heart.

Figure 8:
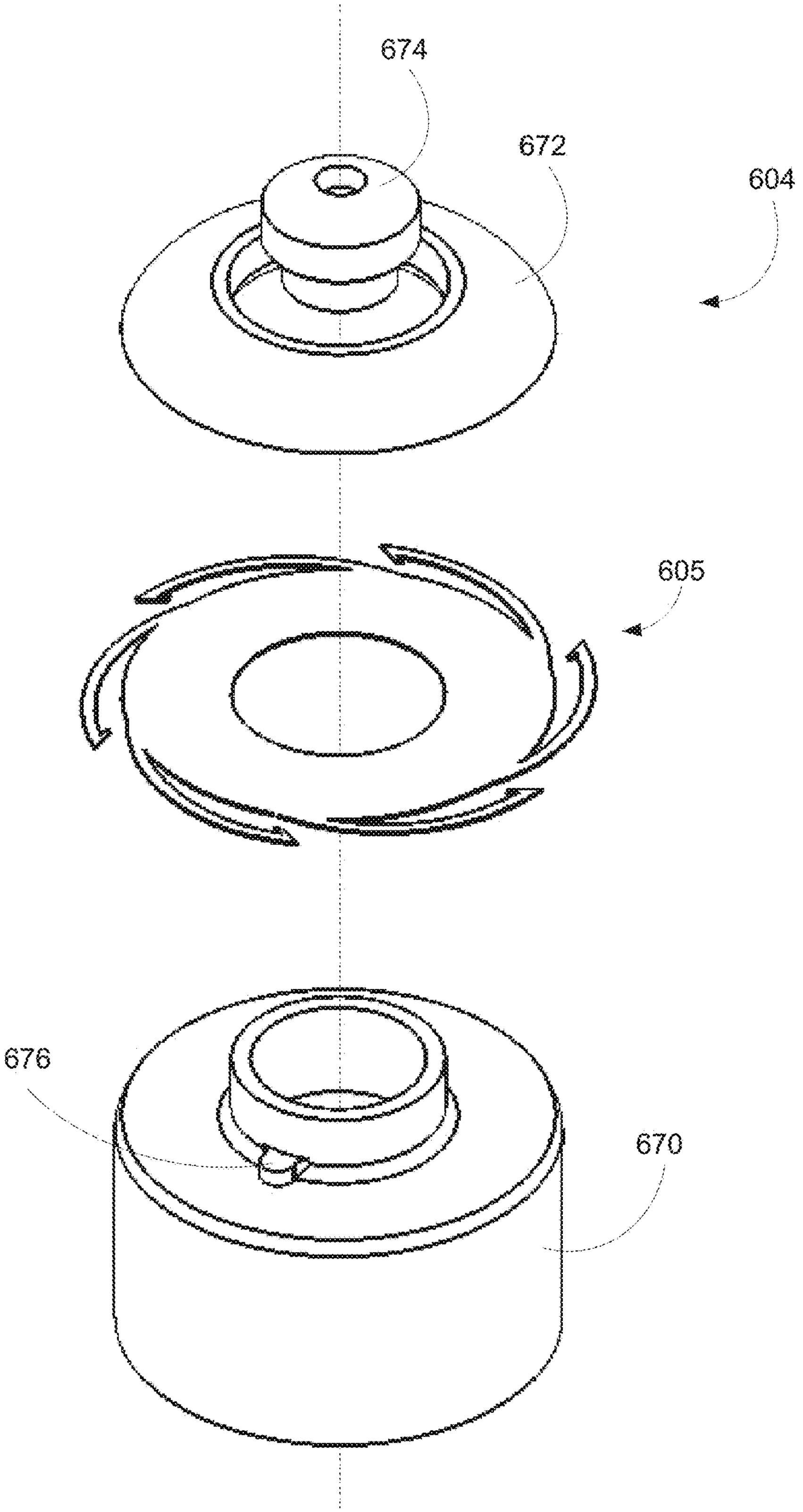
FIG. 8 is an exploded view of a distal assembly of the biostimulator of FIGS. 6-7, in accordance with an embodiment.

FIG. 8 is an exploded view of the header assembly 604 of FIGS. 6 and 7. As illustrated, the header assembly 604 may include a header body 670 and a header cap 672 between which the planar fixation feature 605 is disposed. The header assembly 604 may further include an electrode 674 for delivering pacing or other impulses to the heart tissue.

As shown in FIG. 8, the planar fixation feature 605 may be retained between the header cap 672 and the header body 670. In certain implementations, for example, the planar fixation feature 605 may be coupled to one or both of the header body 670 and the header cap 672 using ultrasonic welding, an adhesive, or other coupling method. The header body 670 may also include a key or similar alignment feature 676 that may be used to facilitate alignment of one or both of the header cap 672 and the planar fixation feature 605. For example, one or both of the header cap 672 and the planar fixation feature 605 may include a notch or similar indentation (not illustrated) corresponding to the key 676 such that, when assembled, one or both of the header cap 672 and the planar fixation feature 605 are in a predetermined orientation.

During implantation, the leadless biostimulator 600 is disposed in proximity to an implantation location and then rotated in a screwing direction (which, in the case of the leadless biostimulator 600 is a clockwise direction but may be counterclockwise in other implementations) causing one or more of the arms 660A-660F to engage the wall of the heart. During rotation in the screwing direction, the barbs 664A-664F of the arms 660A-660F are angled away from the screwing direction of rotation and, in certain implementations, may flatten against the arms 660A-660F so as to not obstruct implantation of the leadless biostimulator 600. As one or more of the arms 660A-660F engages and penetrates the endocardium, the corresponding barb similarly penetrates into the wall of the heart. As the length of the barbs 664A-664F is only a fraction of the total length of their respective arms 660A-660F, full engagement of a curvate arm results in the corresponding barb being fully inserted into through the endocardial layer. Following implantation of the leadless biostimulator 600, counter rotation of the leadless biostimulator 600, such as resulting from natural heart movement, results in the barb engaging the tissue to resist the counter rotation and maintain the leadless biostimulator 600 in engagement with the wall of the heart.

The barbs 664A-664F are generally configured to resist regular counter-torques applied to the leadless biostimulator 600 during normal cardiac activity. However, the barbs 664A-664F may also be designed to deform in the event that removal or repositioning of the leadless biostimulator 600 is required. In other words, while the barbs 664A-664F are sufficiently rigid to oppose regular counter torques, they are also sufficiently pliable such that by applying a sufficient counter-torque (such as by using a delivery or retrieval catheter), the barbs 664A-664F may be made to disengage from the wall of the heart with relatively minimal damage to the surrounding tissue.

In certain implementations, the first counter torque (i.e., the counter torque that the barbs 664A-664F are designed to substantially withstand) may be in a range up to and including 0.5 oz-in. The second counter torque, in contrast, may generally correspond to a predetermined force required to be applied by a retrieval catheter or similar retrieval system that may be used to retrieve/remove the biostimulator 600 following implantation. In such implementations, the second counter torque may be from and including 0.5 oz-in to and including 2.0 oz-in, for example. As described above, the second counter torque can be higher, e.g., by a scale factor, than the first counter torque.

Figure 9A:
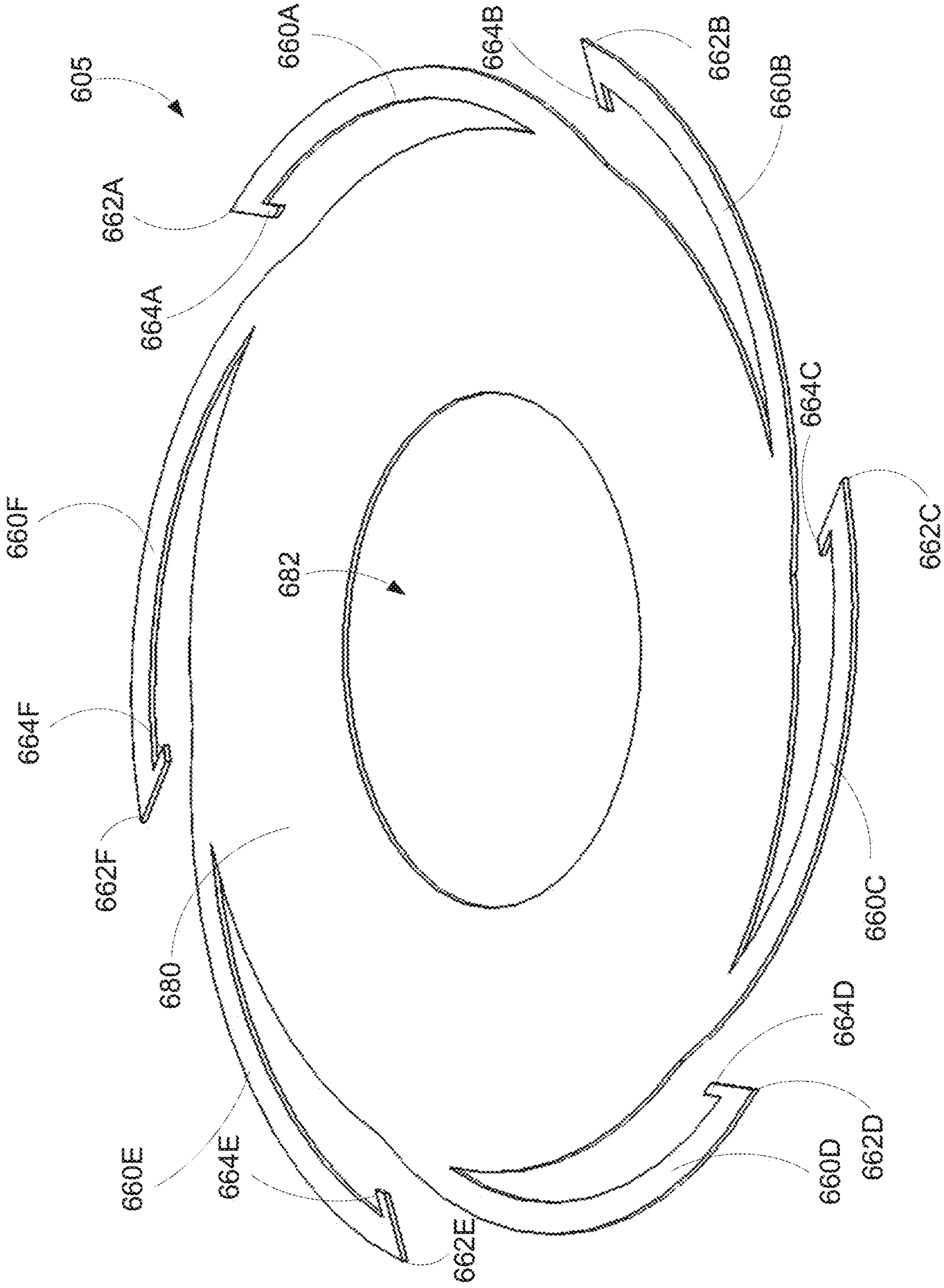
FIG. 9A is an isometric view of the planar fixation feature of FIGS. 6-8, in accordance with an embodiment.
Figure 9B:
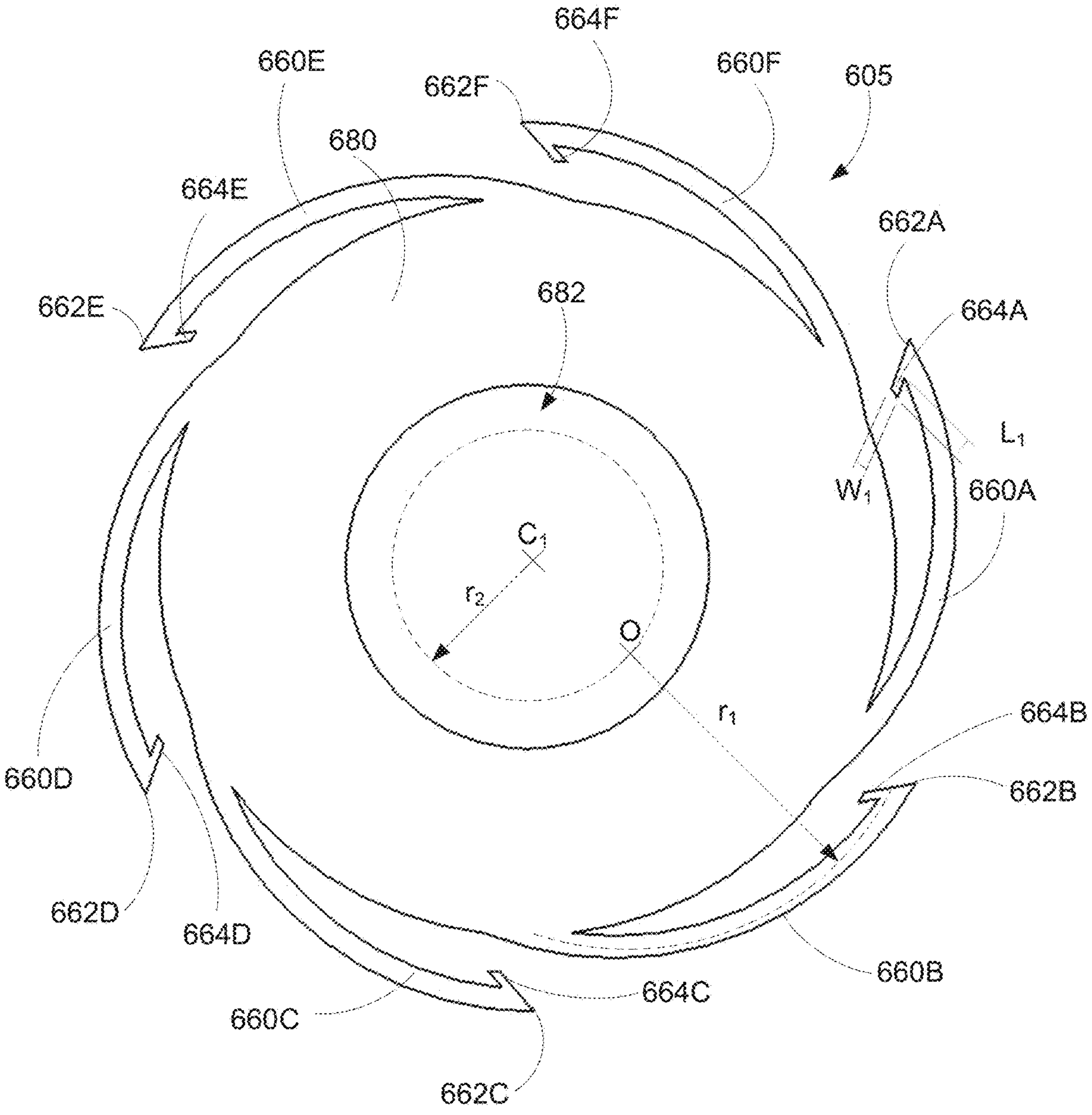
FIG. 9B-9C are distal and side elevation views, respectively, of the planar fixation feature of FIG. 9A, in accordance with an embodiment.
Figure 9C:

FIGS. 9A-9C illustrate the example planar fixation feature 605 in further detail. More specifically, FIG. 9A is an isometric view of the planar fixation feature 605, FIG. 9B is a distal view of the planar fixation feature 605, and FIG. 9C is a side elevation view of the planar fixation feature 605.

As illustrated in FIGS. 9A-9C, the planar fixation feature includes a circular body 680 from which arms 660A-660F extend. Each of the arms 660A-660F extends in a first, screwing direction and terminates in a respective barb 664A-664F extending in a second direction opposite the first direction. The circular body 680 further defines a through hole 682 for coupling the planar fixation feature 605 to other components of a header assembly of a leadless biostimulator, such as the header assembly 604 illustrated in FIG. 8. For example, the through hole 682 may be shaped to receive a protrusion or extension of the header body 670. As previously discussed, the edge of the through hole 682 may further define a notch or protrusion shaped to mate with a corresponding protrusion or notch, respectively, of the header body 670. By doing so, the planar fixation feature

605 may be placed in a predetermined orientation relative to the header body 670 during assembly.

The arms 660A-660F of the planar fixation feature 605 may conform to a predetermined shape or arrangement and have a predetermined geometry. For example, as illustrated in FIG. 9B, each of the arms 660A-660F extends from the circular body 680 along a circular path. With specific reference to arm 660B, each of the arms 660A-660F may be defined by a radius $r_1$ extending from a respective origin O. As shown in FIG. 9B, the origin O may be disposed on a circle defined by a second radius $r_2$ extending from a center $C_1$ of the circular body 680. In certain implementations, the radius $r_1$ may be constant such that the arm 660B extends along a circular arc. In other implementations, the radius $r_1$ may increase along the length of the arm 660B such that the arm 660B follows a spiraling path instead. In one specific example of a planar fixation feature, each arm may have a value of $r_1$ from and including 0.05 inches to and including 0.10 inches and a value of $r_2$ from and including 0.02 inches to and including 0.03 inches. Each of the barbs 664A-664F may also conform to one or more predetermined dimensions. For example, with reference to barb 664A, each barb may have an extension length $L_1$, corresponding to the maximum distance the barb extends from its respective arm, and a width $W_1$. In certain implementations, the extension length $L_1$ may be from and including 0.002 inches to and including 0.01 inches and the width $W_1$ may be from and including 0.001 inches to and including 0.005 inches. Notably, the arms 660A-660F need not be curvate provided they extend in a screwing direction of the leadless biostimulator 600. For example, in contrast to the foregoing implementations, the planar fixation feature 605 may instead include substantially straight arms that extend from the circular body 680. Such straight arms may extend, for example, at an angle tangential to the outer extent of the circular body 680.

As illustrated in FIG. 9C, the planar fixation feature 605 is substantially flat and is generally formed from a thin sheet of material. In certain implementations, the planar fixation feature 605 may be formed from a sheet or film having a thickness 684 from and including 0.001 inches to and including 0.010 inches. For example, in one method of manufacturing the planar fixation feature 605, a sheet or film may be formed using a film converting process. The sheet/film may then be punched, cut, trimmed, or otherwise processed to produce the planar fixation feature 605.

To achieve the required characteristics of the barbs 664A-664F, the planar fixation feature 605 may be formed from a flexible plastic material, such as polyimide. In other implementations, the planar fixation feature 605 may instead be formed of other flexible biocompatible materials including, without limitation, one or more of polyester, polyethylene, polypropylene, polyurethane, polyether ether ketone (PEEK), or polyvinylidene fluoride. Material selection for the planar fixation feature 605 may alternatively be based on particular properties or characteristics of the material. In certain implementations, the planar fixation feature may be formed from one or more bioabsorbable materials, as described above. For example, the bioabsorbable material(s) may include a magnesium alloy. In certain implementations, the planar fixation feature 605 may be formed from a material having a Young's modulus from and including 0.5 GPa to and including 10 GPa. Material selection for the planar fixation feature 605 may alternatively be based on material toughness which is often associated with specific tensile and compression strengths of the material.

As illustrated in the preceding figures, the planar fixation feature 605 may include six arms 660A-660F. In alternative implementations, however, the planar fixation feature 605 may include more or fewer than six arms. For example, and without limitation, implementations of planar fixation features according to the present disclosure may include from one to six or more arms. Also, while each of the arms 660A-660F is illustrated in FIGS. 6-9C as being substantially the same, each arm may vary in its length and shape. For example and without limitation, some or all of the arms of planar fixation features according to this disclosure may have different lengths, different barb shapes and/or barb lengths, follow different curvatures, or have no curvature at all in the case of straight arms.

C. Leadless Biostimulator with a Forward-Facing Fixation Structure Including Integrated Primary and Secondary Fixation Features As previously discussed in the context of FIG. 2, certain implantation locations within the heart (such as in the vicinity of the apex of the heart) have geometries that may present challenges to proper implantation of a leadless biostimulator. To overcome this issue, biostimulators in accordance with this disclosure may include forward-facing primary and secondary fixation features. In the implementation of FIG. 2, for example, the primary fixation feature is in the form of a primary wire helix while the secondary fixation feature, which resists counter-rotation following implantation, is in the form of one or more forward-facing sutures extending from a distal end of the leadless biostimulator. More specifically, the forward-facing sutures extend from a distal end of the leadless biostimulator about which the primary fixation helix extends.

To improve engagement of the secondary fixation feature, implementations of the present disclosure also include designs in which the secondary fixation feature is in proximity to the engagement point of the primary fixation feature. In the implementation of FIGS. 4-5B, for example, the secondary fixation feature is a sleeve disposed near the tip of the primary helix. In the implementation of FIGS. 6-9C, the primary and secondary fixation features are integrated into a unitary planar fixation feature that extends laterally from the distal end to the leadless biostimulator. Notably, the unitary design of FIGS. 6-9C provides benefits related to manufacturing efficiency and reduced costs.

The following disclosure is directed to yet another implementation of a leadless biostimulator that includes primary and secondary fixation features. Similar to the previous example implementations, the primary fixation feature generally extends in a first, screwing direction to fix the leadless biostimulator to a wall of the heart. Once implanted, the secondary fixation feature resists counter rotation of the leadless biostimulator such that regular cardiac activity does not result in dislodgment of the leadless biostimulator. In contrast to the previous designs, however, the following disclosure is directed to a fixation structure that provides the implantation advantages of a forward-facing fixation feature arrangement with the improved manufacturability and engagement provided by a unitary fixation structure that incorporates both primary and secondary fixation features.

More specifically, a leadless biostimulator is provided that includes a forward-facing fixation structure including several arms that extend from the distal end of the leadless biostimulator. Each of the arms extends in a first or screwing direction. For example, the arms may be biased at an angle or extend helically about a longitudinal axis of the leadless biostimulator. Implantation is therefore achieved by disposing the distal ends of the arms in contact with the wall of the heart and rotating the leadless biostimulator in the screwing direction.

Disposed at the end of each arm is a hook, barb, or similar secondary fixation feature that points in a direction substantially opposite the screwing direction. Accordingly, after the leadless biostimulator has been implanted, counter-torques experienced by the leadless biostimulator (such as those resulting from normal cardiac activity) are resisted by the secondary fixation features.

The following fixation structure has various advantages. Among other things, the placement of the secondary fixation features adjacent to the tips of the primary fixation ensures that the secondary fixation features are able to engage the wall of the heart with relatively minimal engagement of the primary fixation features. Also, the unitary design of the fixation structure simplifies manufacturing of the fixation structure and improves manufacturing tolerances. For example, the fixation structure may be machined or otherwise cut from a tubular structure that may be made by extrusion or a similar process. By doing so, the manufacturing process is less complicated as compared to conventional fixation mechanisms and the thickness of the tubular structure can be tightly controlled to impart specific performance characteristics on the fixation structure. Additional implementations and benefits of those implementations will become apparent in light of the following disclosure, which provides an example leadless biostimulator and fixation structure according to the present disclosure.

Figure 10:
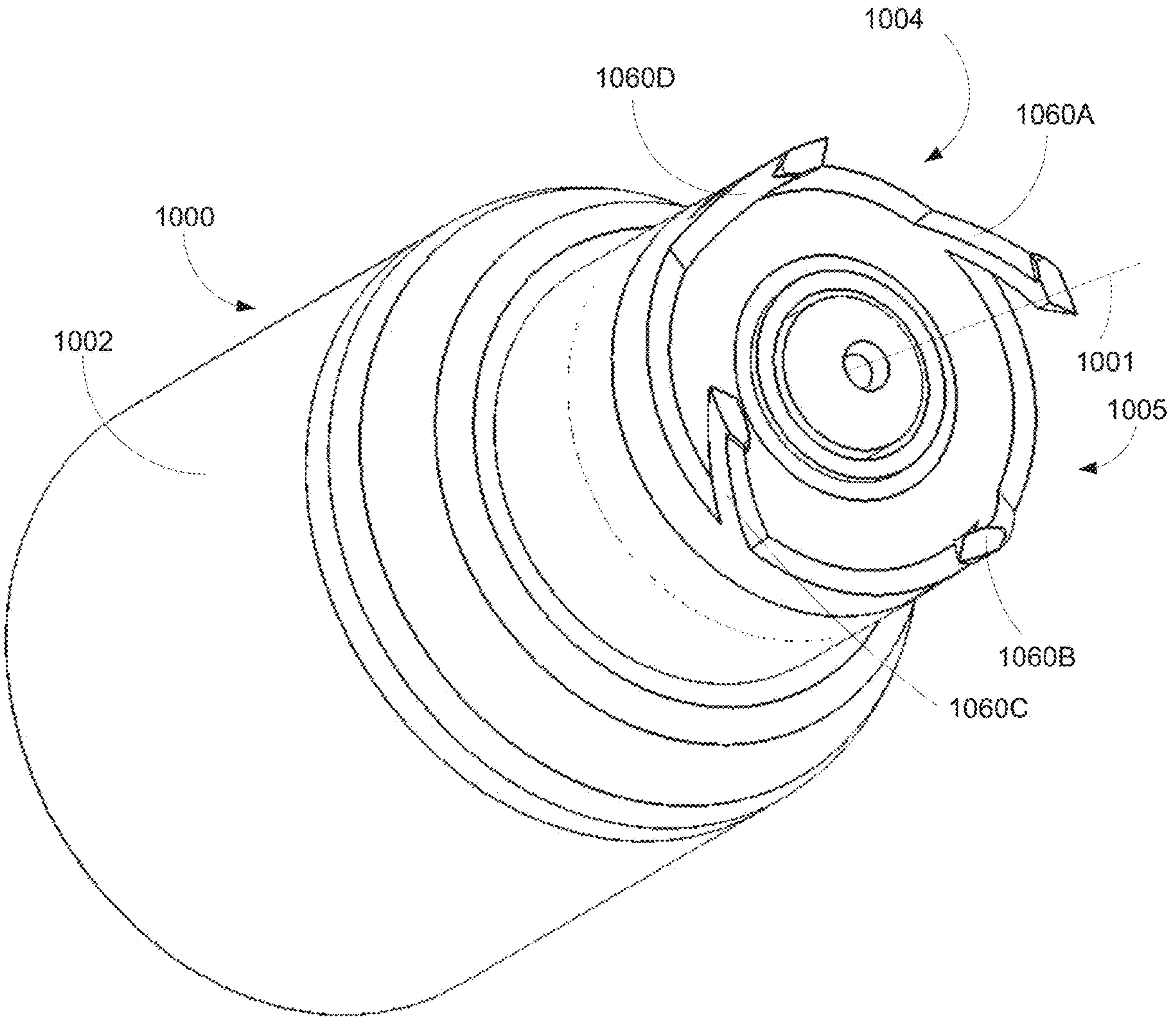
FIGS. 10-11 are isometric views of a fourth biostimulator including a forward facing fixation feature, in accordance with an embodiment.
Figure 11:
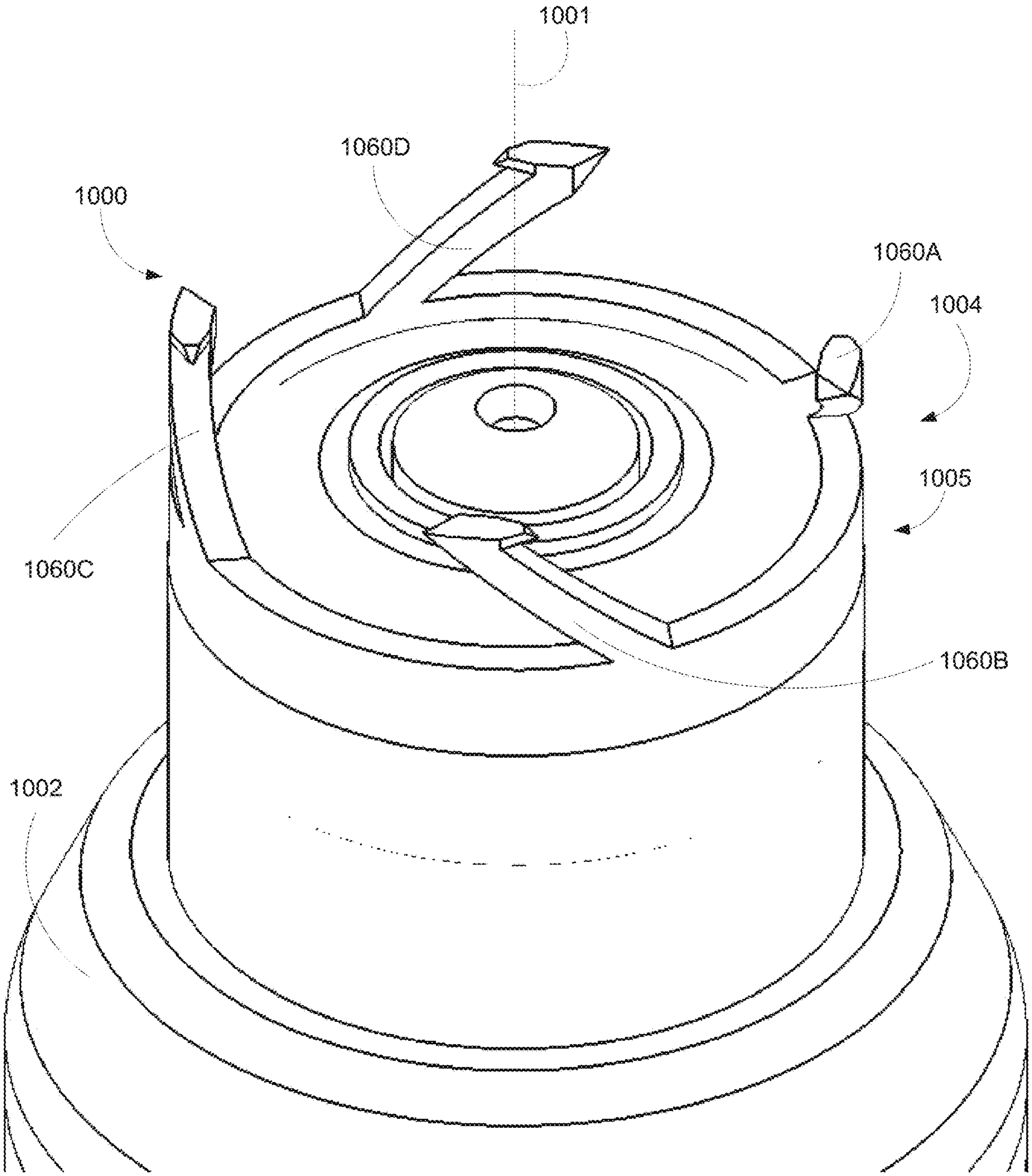

FIGS. 10 and 11 are isometric views of a biostimulator 1000 in accordance with the present disclosure. The biostimulator 1000 includes a housing 1002 and a header assembly 1004 coupled thereto. Coupling of the housing 1002 to the header assembly 1004 may be accomplished in various ways including, without limitation, one or more of a biocompatible adhesive, a threaded connection, and ultrasonic welding.

The header assembly 1004 includes a fixation feature 1005 extending from a distal end of the header assembly 1004. In contrast to the laterally extending fixation feature 605 of FIGS. 6-9C, the fixation feature 1005 of the leadless biostimulator 1000 extends in a longitudinal direction from a distal end of the leadless biostimulator 1000 about a longitudinal axis 1001 of the leadless biostimulator 1000. The fixation feature 1005 includes several arms 1060A-1060D for fixation of the leadless biostimulator 1000 to a wall of the heart.

The arms 1060A-1060D provide both primary fixation functionality by enabling implantation of the leadless biostimulator 1000 into the wall of the heart and secondary fixation functionality by resisting counter-rotation of the leadless biostimulator 1000 following implantation. To do so, each of the arms 1060A-1060D extends in a first or screwing direction and terminates in a respective point 1062A-1062D (indicated in FIG. 13A). Accordingly, when the biostimulator 1000 is brought into contact with a wall of the heart and rotated in the first direction, the arms 1060A-1060D engage and implant into the wall of the heart.

The arms 1060A-1060D further include respective barbs 1064A-1064D (indicated in FIG. 13A) or similar anti-rotation feature extending in a second or unscrewing direction opposite the screwing direction. Accordingly, once implanted, the barbs 1064A-1064D provide resistance to counter-torques that may arise from movement of the patient or cardiac activity and that may otherwise cause loosening and/or disengagement of the leadless biostimulator 1000 from the wall of the heart.

The barbs 1064A-1064D are generally configured to resist regular counter-torques applied to the leadless biostimulator 1000 during normal cardiac activity. However, the barbs 1064A-1064D may also be designed to deform in the event that removal or repositioning of the leadless biostimulator 1000 is required. In other words, while the barbs 1064A-1064D are sufficiently rigid to oppose regular counter torques, they are also sufficiently pliable such that by applying a sufficient counter-torque (such as by using a delivery or retrieval catheter), the barbs 1064A-1064D may be made to disengage from the wall of the heart with relatively minimal damage to the surrounding tissue.

In certain implementations, the first counter torque (i.e., the counter torque that the barbs 1064A-1064D are designed to substantially withstand) may be in a range up to and including 0.5 oz-in. The second counter torque, in contrast, may generally correspond to a predetermined force required to be applied by a retrieval catheter or similar retrieval system that may be used to retrieve/remove the biostimulator 1000 following implantation. In such implementations, the second counter torque may be from and including 0.5 oz-in to and including 2.0 oz-in, for example. As described above, the second counter torque can be higher, e.g., by a scale factor, than the first counter torque.

To achieve the required characteristics of the barbs 1064A-1064D, the fixation feature 1005 may be formed from a flexible plastic material, such as polyimide. In other implementations, the fixation feature 1005 may instead be formed of other flexible biocompatible materials including, without limitation, one or more of polyester, polyethylene, polypropylene, polyurethane, polyether ether ketone (PEEK), or polyvinylidene fluoride. Material selection for the fixation feature 1005 may alternatively be based on particular properties or characteristics of the material. In certain implementations, the fixation feature may be formed from one or more bioabsorbable materials, as described above. For example, the bioabsorbable material(s) may include a magnesium alloy. In certain implementations, the planar fixation feature 1005 may be formed from a material having a Young's modulus from and including 0.5 GPa to and including 10 GPa. Material selection for the fixation feature 1005 may alternatively be based on material toughness which is often associated with specific tensile and compression strengths of the material.

Figure 12:
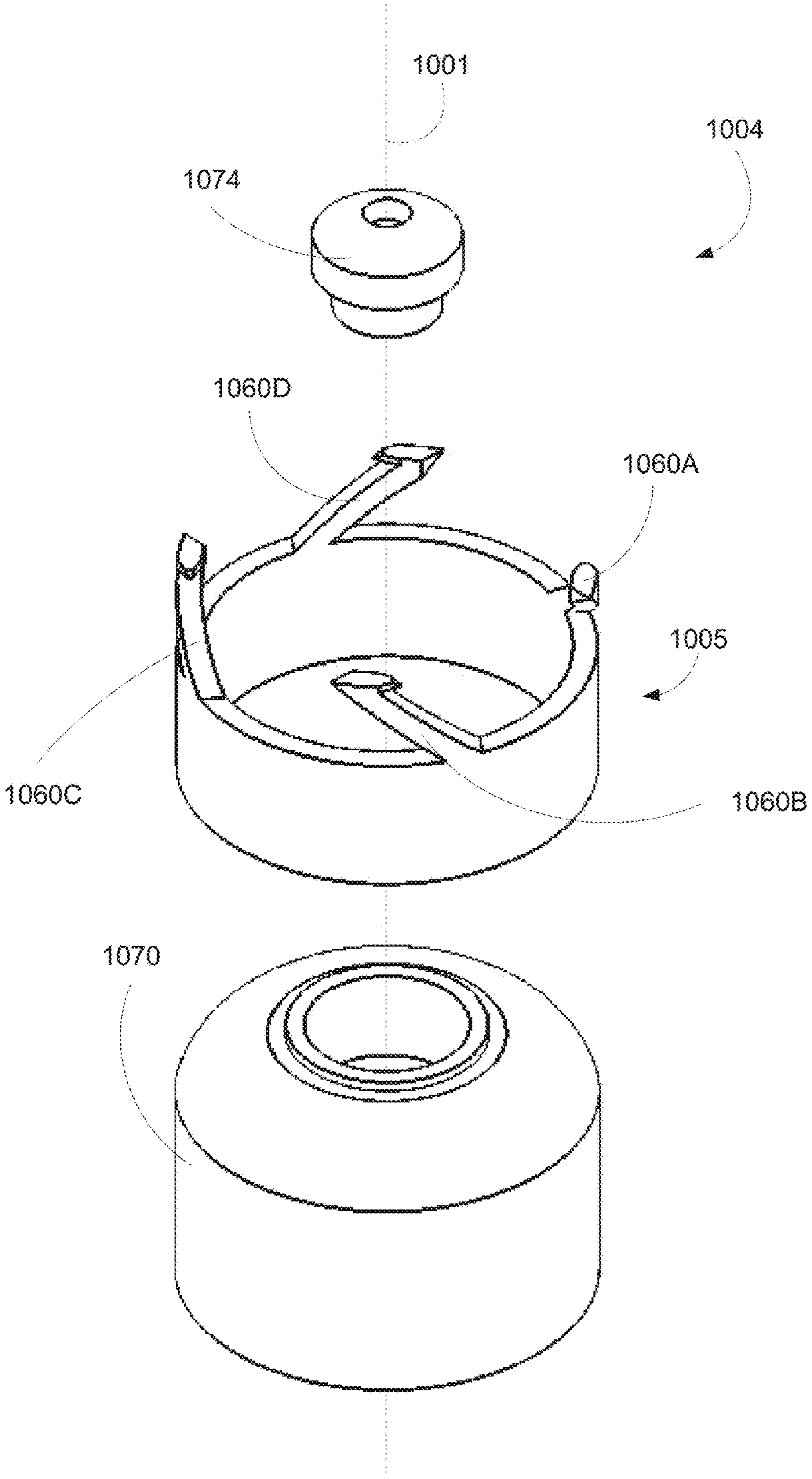
FIG. 12 is an exploded view of a distal assembly of the biostimulator of FIGS. 10-11, in accordance with an embodiment.

FIG. 12 is an exploded view of the header assembly 1004 of FIGS. 10 and 11. As illustrated, the header assembly 1004 may include a header body 1070 about which the fixation feature 1005 is disposed. The header assembly 1004 may further include an electrode 1074 for delivering pacing or other impulses to the heart tissue. The fixation feature 1005 may be coupled to the header body 1070 using various methods including, without limitation, one or more of a threaded connection, an adhesive, ultrasonic or other welding, a fastener (such as a set screw), or any other suitable coupling method. The header body 1070 and the fixation feature 1005 may also include mating features, such as corresponding slots and keys, to ensure alignment of the header body 1070 and the fixation feature 1005.

Figure 13A:
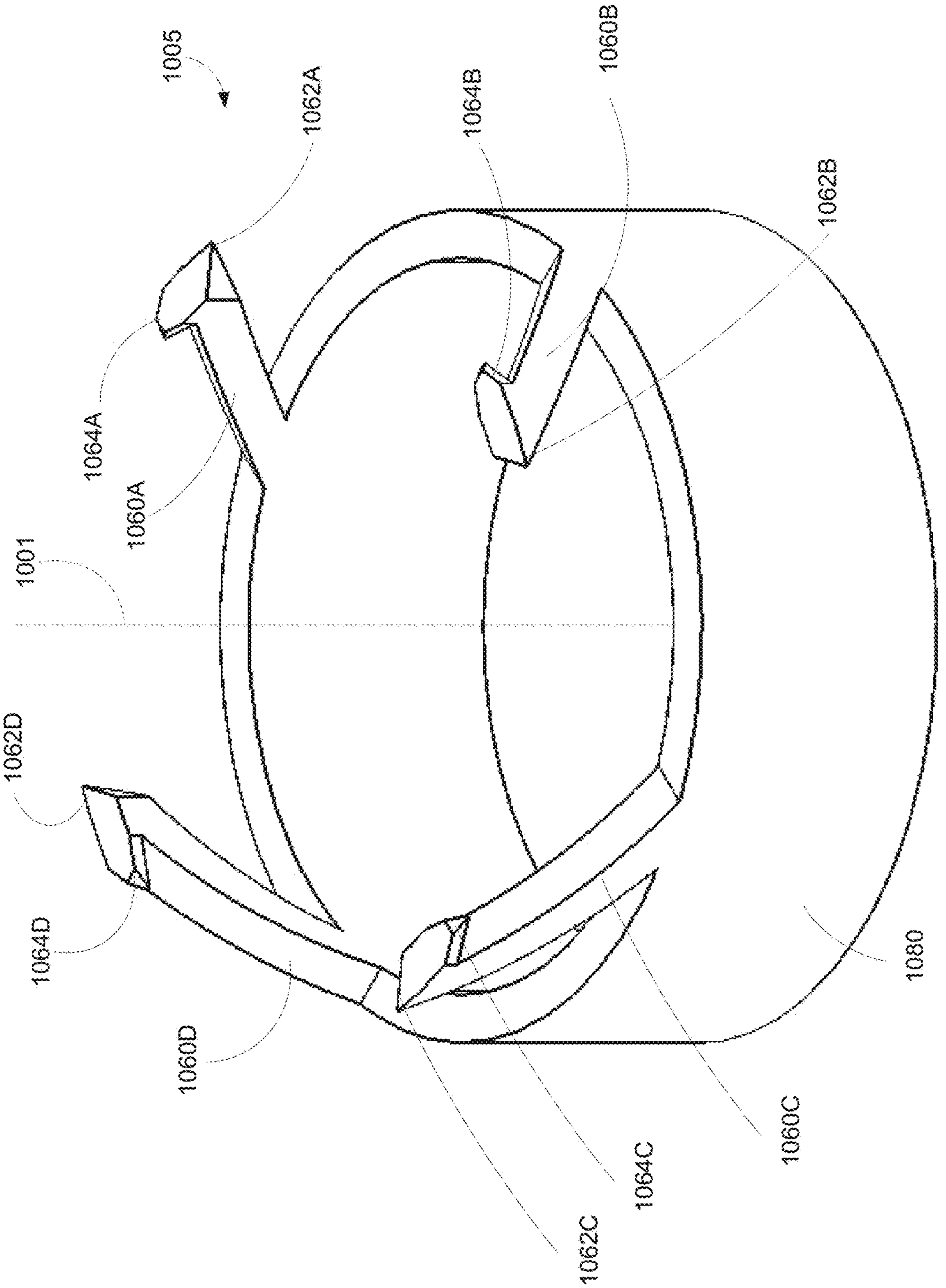
FIG. 13A is an isometric view of the forward facing fixation feature of FIGS. 10-12, in accordance with an embodiment.
Figure 13B:
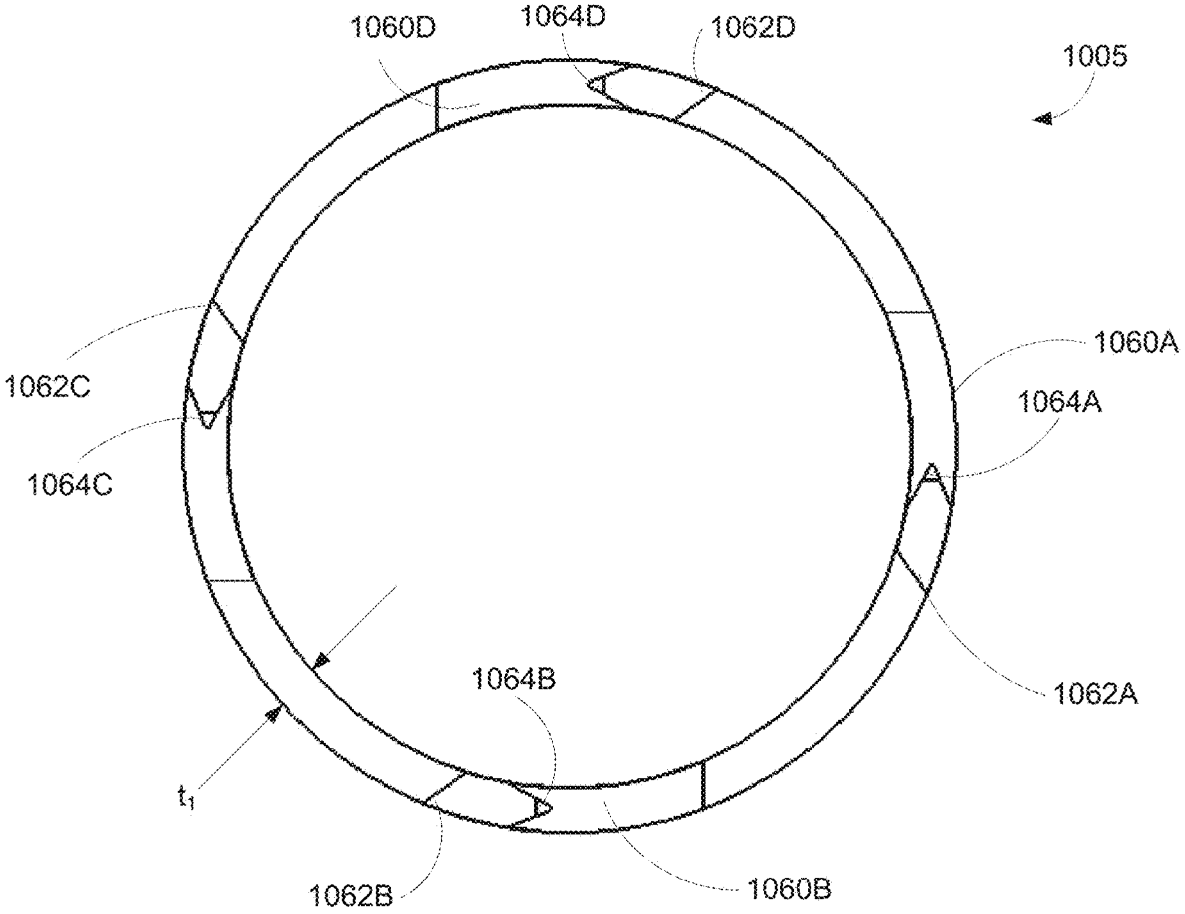
FIG. 13B-13C are distal and side elevation views, respectively, of the planar fixation feature of FIG. 13A, in accordance with an embodiment.
Figure 13C:
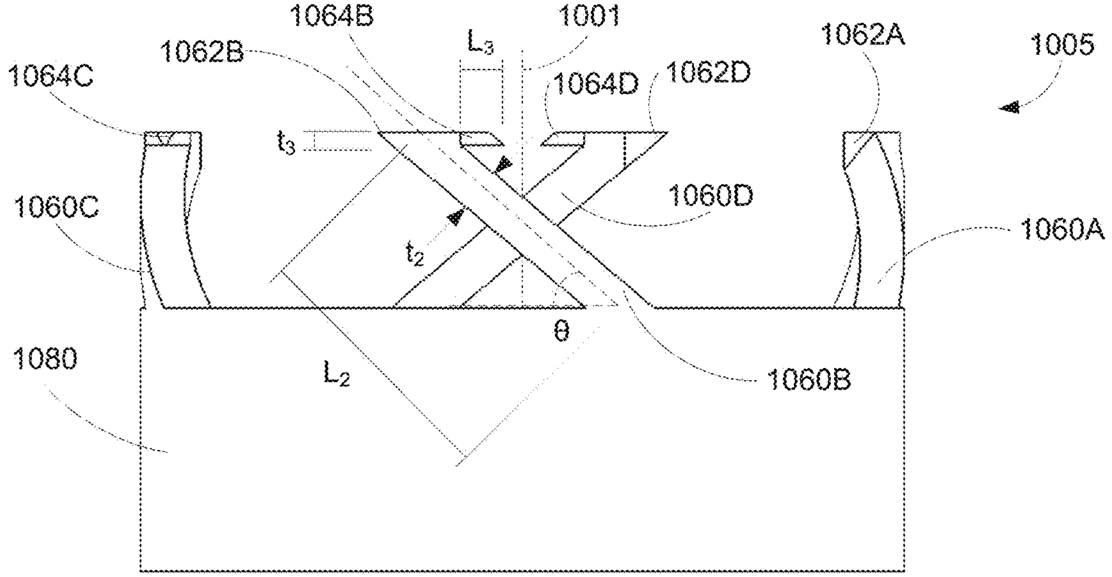

FIGS. 13A-13C illustrate the example fixation feature 1005 in further detail. More specifically, FIG. 13A is an isometric view of the fixation feature 1005, FIG. 13B is a distal view of the fixation feature 1005, and FIG. 13C is a side elevation view of the fixation feature 1005.

As illustrated in FIGS. 13A-13C, the fixation feature 1005 includes a cylindrical body 1080 from which arms 1060A-1060D extend. Each of the arms 1060A-1060D extend in a first, screwing direction and terminates in a respective barb 1064A-1064D extending in a second direction opposite the first direction. As previously discussed in the context of FIG. 12, the cylindrical body 1080 is shaped to be disposed about and coupled to a header body of the biostimulator. As previously discussed, the interior surface of the cylindrical body 1080 may include a protrusion, slot, or similar feature, that engages with a corresponding feature of the header body 1070 to align the cylindrical body 1080 relative to the header body 1070.

The tubular structure of the fixation feature 1005 is most evident in FIG. 13B, which is a distal view of the fixation feature 1005. As illustrated, each of the cylindrical body 1080 and each of the arms 1060A-1060D are formed from a uniform tubular structure having a thickness $t_1$. For example, the fixation feature 1005 may be formed from an extruded or similarly formed tube that is then cut (such as by die cutting, laser cutting, and the like) to form the arms 1060A-1060D and their respective primary and secondary fixation features. Using the extrusion process, the thickness $t_1$ can be tightly controlled as can the flexibility of the arms 1060A-1060D.

As shown in FIG. 13C, the arms 1060A-1060D of the fixation feature 1005 may conform to a predetermined shape or arrangement and have a predetermined geometry. With reference to FIG. 13C, various dimensional aspects of the arm 1060B are illustrated that are representative of the other arms of the fixation feature 1005. A first parameter of the arm 1060B that may be controlled to vary performance of the fixation feature 1005 is the pitch angle θ of the arm 1060B. The pitch angle θ generally dictates the "aggressiveness" of the arm 1060B and how readily the arm 1060B engages the wall of the heart. In certain implementations, the θ of the arm 1060B may be from and including 15 degrees to and including 60 degrees. The arm thickness $t_2$ may also be varied to change the rigidity and corresponding performance characteristics of the arms 1060B. In certain implementations, the arm thickness $t_2$ may be from and including 0.005 inches to and including 0.030 inches. The arm 1068B may be further defined by an arm length $L_2$. In certain implementations, the arm length $L_2$ may be from and including 0.010 inches to and including 0.200 inches.

The barbs 1064A-1064D may also conform to predetermined dimensions and geometries. For example, as illustrated in FIG. 13C, each barb may have a barb length $L_3$ that from and including 0.005 inches to and including 0.200 inches. The barbs 1064A-1064D may also have a barb thickness $t_3$ from and including 0.004 inches to and including 0.030 inches.

As shown in FIG. 13C, the distal extent of the fixation feature 1005 is substantially flat. More specifically, each of the tips 1062A-1062D and the barbs 1064A-1064D extend in a substantially lateral direction. In other implementations, however, each of the tips 1062A-1062D and the barbs 1064A-1064D may instead extend at an angle relative to a lateral plane of the leadless biostimulator. For example, in certain implementations, each of the tips 1062A-1062D may extend in a partially distal direction and each of the barbs 1064A-1064D may extend in a partially proximal direction.

As illustrated in the preceding figures, the fixation feature 1005 may include four arms 1060A-1060D. In alternative implementations, however, the fixation feature 1005 may include more or fewer than four arms. For example, and without limitation, implementations of fixation features according to the present disclosure may include from one to four or more arms. Also, while each of the arms 1060A-1060D is illustrated in FIGS. 10-13C as being substantially the same, each arm may vary in its length, shape, or other characteristics. For example and without limitation, some or all of the arms of planar fixation features according to this disclosure may have different lengths, different barb shapes and/or barb lengths, or have different pitch angles.

D. Leadless Biostimulator with Anti-Rotation Shim

In another implementation of the present disclosure, a leadless biostimulator is provided that includes a conventional primary fixation feature (e.g., a helical wire) but further includes an anti-rotational shim disposed proximal to the tip of the primary fixation feature. The shim provides secondary fixation by resisting counter-rotation of the leadless biostimulator following implantation.

The anti-rotational shim may be formed from any of the biocompatible materials described above, including bioabsorbable polymers or metals. In certain implementations, the shim may be formed from converted plastic thin film sheets or other thin film material. The sheet is then cut or otherwise shaped to form flexible barbs that extend laterally from the biostimulator in a direction opposite that of the screwing direction of the primary fixation helix. In certain implementations, for example, the barb features are cut out of the sheet in a circular disc pattern to form a shim. The cut shim is then placed over a helix mount and held in place by a helix mount cap. The cap may be held in place by an adhesive, ultrasonic welding, ultrasonic staking, or other bonding method. In such an implementation, the shim may be disposed between windings of the primary fixation helix. By doing so, the barb features are optimally placed to prevent counter-rotation of the leadless pacemaker (i.e., rotation in an unscrewing direction) after implantation and to also be displaced relative to a stimulation electrode of the leadless biostimulator.

The geometric profile of the shim, including the thickness of the sheet from which the shim is formed, is chosen such that the barb can pierce the endocardium when the leadless biostimulator is subjected to a relatively small counter-torque. However, by applying reasonable overload torque the barbs give way and bend back against themselves, allowing the leadless biostimulator to be unscrewed and repositioned without severely damaging tissue in the implantation area.

Figure 14:
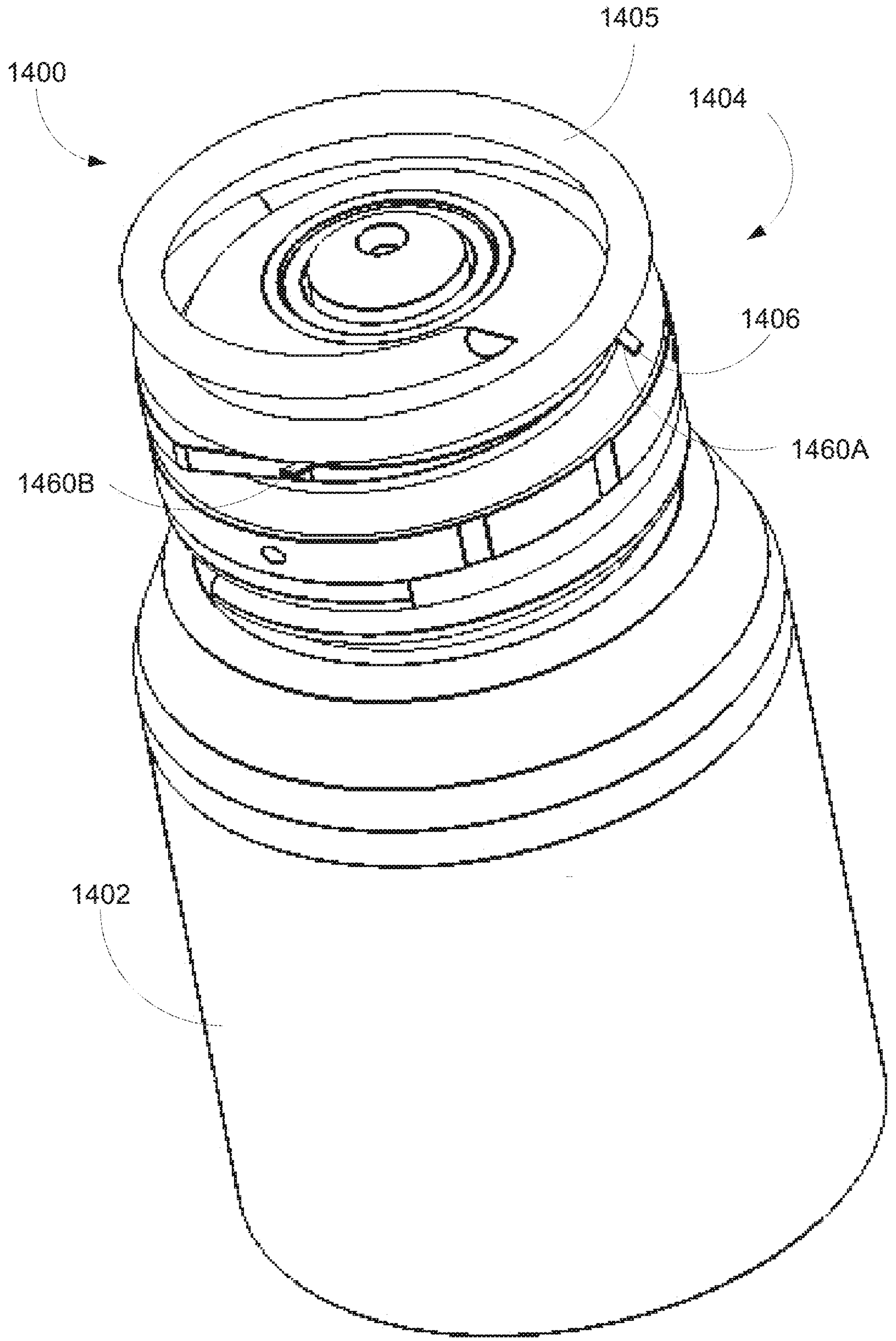
FIGS. 14-15 are isometric views of a fourth biostimulator in accordance with the present disclosure and including a primary fixation helix and a planar secondary fixation feature, in accordance with an embodiment.
Figure 15:
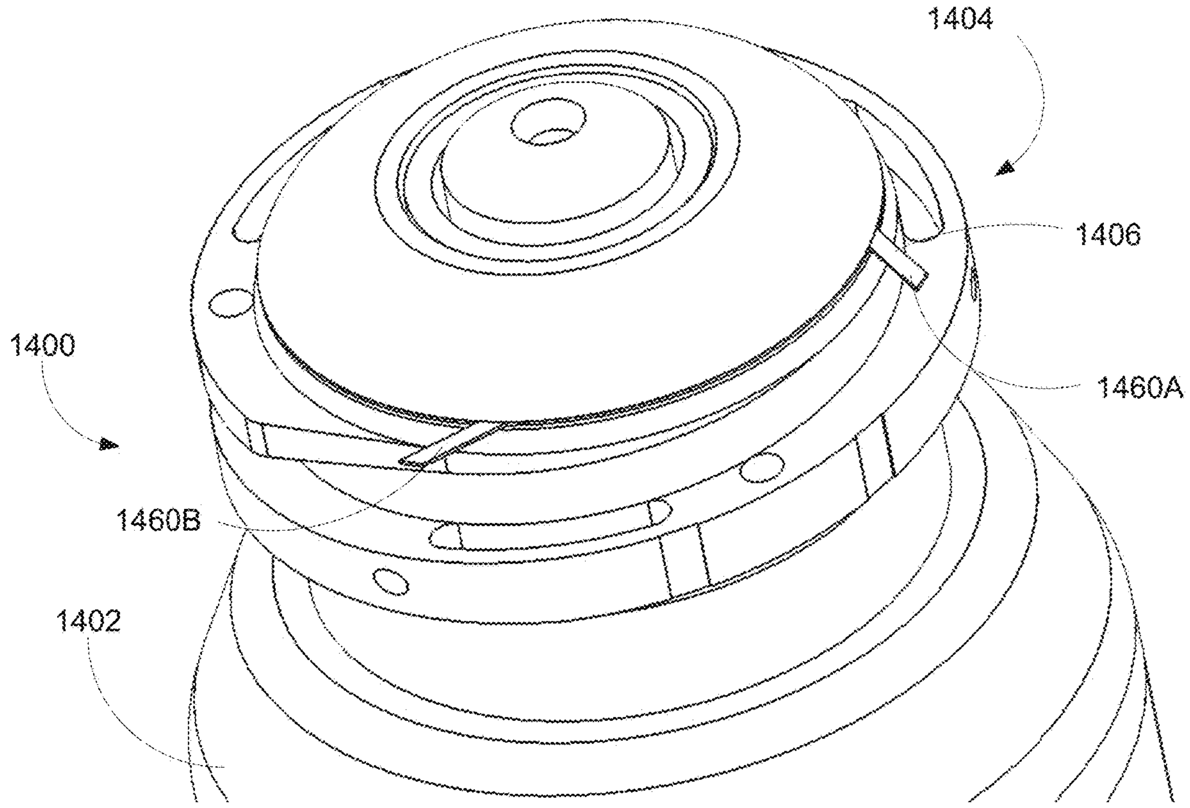

FIGS. 14 and 15 are isometric views of a biostimulator 1400 in accordance with the present disclosure. The biostimulator 1400 includes a housing 1402 and a header assembly 1404 coupled thereto. Coupling of the housing 1402 to the header assembly 1404 may be accomplished in various ways including, without limitation, one or more of a biocompatible adhesive, a threaded connection, and ultrasonic welding.

The header assembly 1404 generally includes a primary fixation feature 1405, and a secondary fixation feature 1406 laterally extending from the leadless biostimulator 1400. In general, the secondary fixation feature 1406 functions as an anti-unscrewing feature that resists unscrewing of the biostimulator 1400 after implantation. In the specific example of FIG. 14, the primary fixation device 1405 is a primary helix 1405 pointing in a first direction. For clarity and to illustrate other components of the biostimulator 1400, the primary fixation device 1405 is removed in FIG. 15. The secondary fixation feature 1406 is a shim 1406 that includes barbs or arms 1460A-1460B that laterally extend from the biostimulator 1400. As illustrated, the shim 1406 is disposed relative to the primary helix 1405 such that the shim 1406 extends between adjacent windings of the primary helix 1405. In certain implementations, for example, the shim 1406 is positioned relative to the primary helix 1405 such that the barbs 1460A-1460B protrude between the first half most distal turn and the second most distal turn of the primary helix 1405. Characteristics of the primary helix

1405 may be substantially similar to the primary helix 305 discussed in the context of the biostimulator 300 of FIG. 3.

In an embodiment, an outer dimension of the shim 1406 may be larger than an outer dimension of the primary helix 1405. For example, an outer tip of the barbs 1460A-1460B may be radially separated from a central axis of the leadless biostimulator 1400 by a radial distance that is greater than a radial distance separating the primary helix 1405 from the central axis. Accordingly, the shim 1406 can contact tissue radially outward from the helix 1405 when the leadless biostimulator 1400 is engaged with the heart tissue. Such contact allows the shim 1406 to move in one direction and resist movement in another direction, as described below.

As described below in the context of FIGS. 18A-18B, implantation of the leadless biostimulator 1400 includes positioning the leadless biostimulator 1400 at an implantation location adjacent a wall of a chamber of the heart and rotating the leadless biostimulator 1400 in a screwing direction to cause the primary helix 1405 to engage the wall of the heart. After initial insertion of the primary helix 1405, the leadless biostimulator 1400 may be further rotated, such that an electrode 1411 is brought into contact with the wall of the heart. During this process, the barbs of the shim 1406 are brought into proximity with the wall of the heart as well. As a result, when a counter-torque is applied to the leadless biostimulator (such as may occur during normal cardiac activity), the barbs 1460A-1460B may engage the wall of the heart and prevent the leadless biostimulator from becoming dislodged.

The barbs 1460A-1460B may be further adapted to disengage the wall of the heart when a predetermined counter-torque is exceeded. For example, the barbs 1460A-1460B may be formed of a flexible material capable of resisting a first counter torque but if a second counter torque is applied that is greater than the first counter torque, the barbs 1460A-B may deflect, bend, compress, buckle, or otherwise deform such that the barbs 1460A-B are no longer pointed in a direction substantially opposite that of the primary helix 1405. When so deformed, the biostimulator 1400 may be counter rotated to disengage the primary helix 1405, enabling removal and/or repositioning of the biostimulator 300. In certain implementations, the first counter torque may generally correspond to the anticipated counter torque that may be experienced during regular patient activity plus a predetermined safety factor. For example, the first counter torque may be from and including 0 oz-in to and including 0.5 oz-in. In certain implementations, the second counter torque may generally correspond to a predetermined force required to be applied by a retrieval catheter or similar retrieval system that may be used to retrieve/remove the biostimulator 1400 following implantation. In such implementations, the second counter torque may be from and including 0.5 oz-in to and including 2.0 oz-in, for example.

Figure 16:
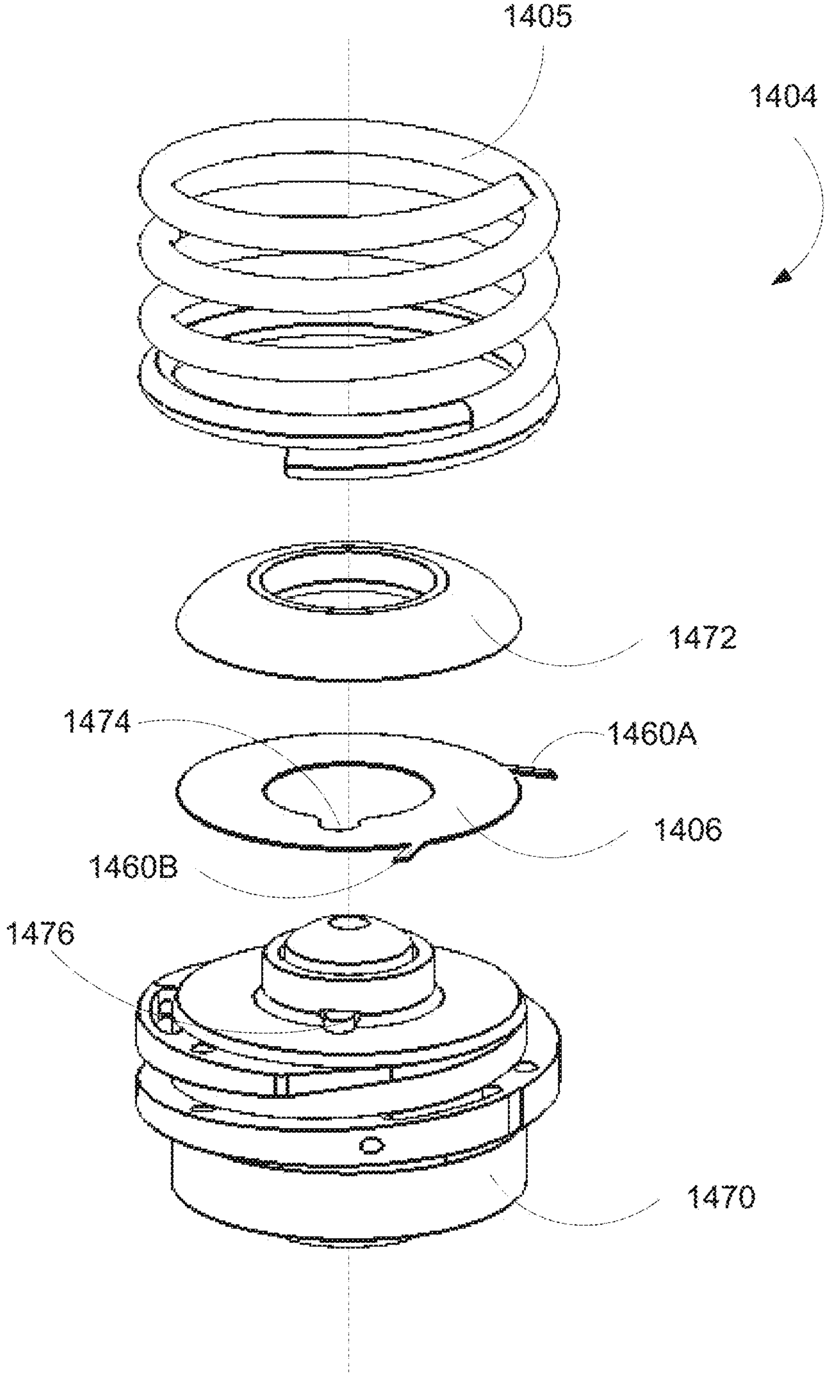
FIG. 16 is an exploded view of a distal assembly of the biostimulator of FIGS. 14-15, in accordance with an embodiment.

FIG. 16 is an exploded view of the header assembly 1404 of FIGS. 14 and 15. As illustrated, the header assembly 1404 may include a header body 1470 and a header cap 1472 between which the shim 1406 is disposed. The header assembly 1404 further includes the electrode 1411 used to delivering pacing or other impulses to the heart tissue. The shim 1406 may be retained between the header cap 1472 and the header body 1470 and may be coupled to one or both of the header body 1470 and the header cap 1472 using ultrasonic welding, an adhesive, or other coupling method. The header body 1470 may also include a key or similar alignment feature 1476 that may facilitate alignment of one or both of the header cap 1472 and the shim 1406. For example, one or both of the header cap 1472 and the shim 1406 may include a notch 1474 or similar indentation corresponding to the key 1476 such that, when assembled, one or both of the header cap 1472 and the shim 1406 are in a predetermined orientation.

Figure 17A:
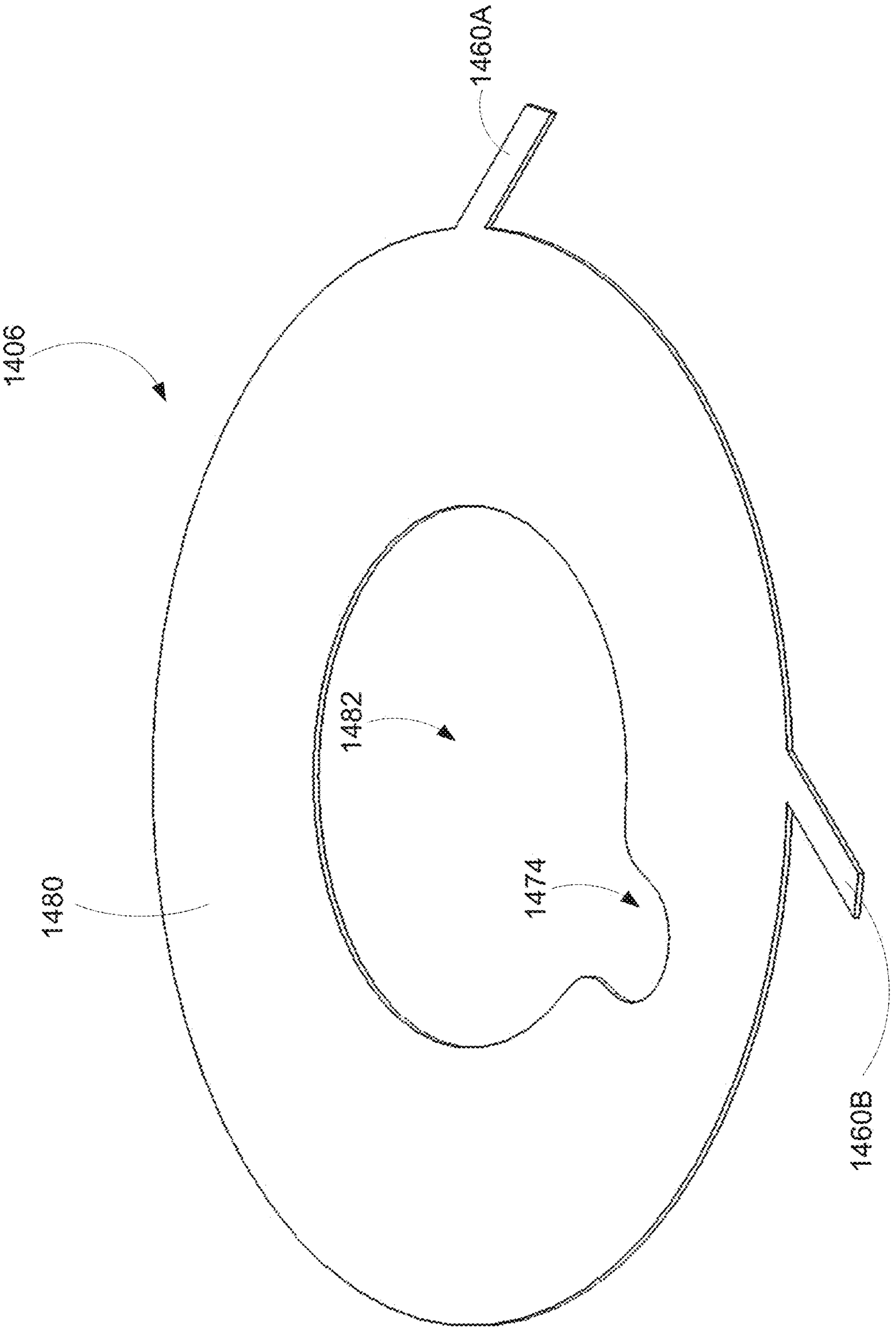
FIG. 17A is an isometric view of the forward facing fixation feature of FIGS. 14-16, in accordance with an embodiment.
Figure 17B:
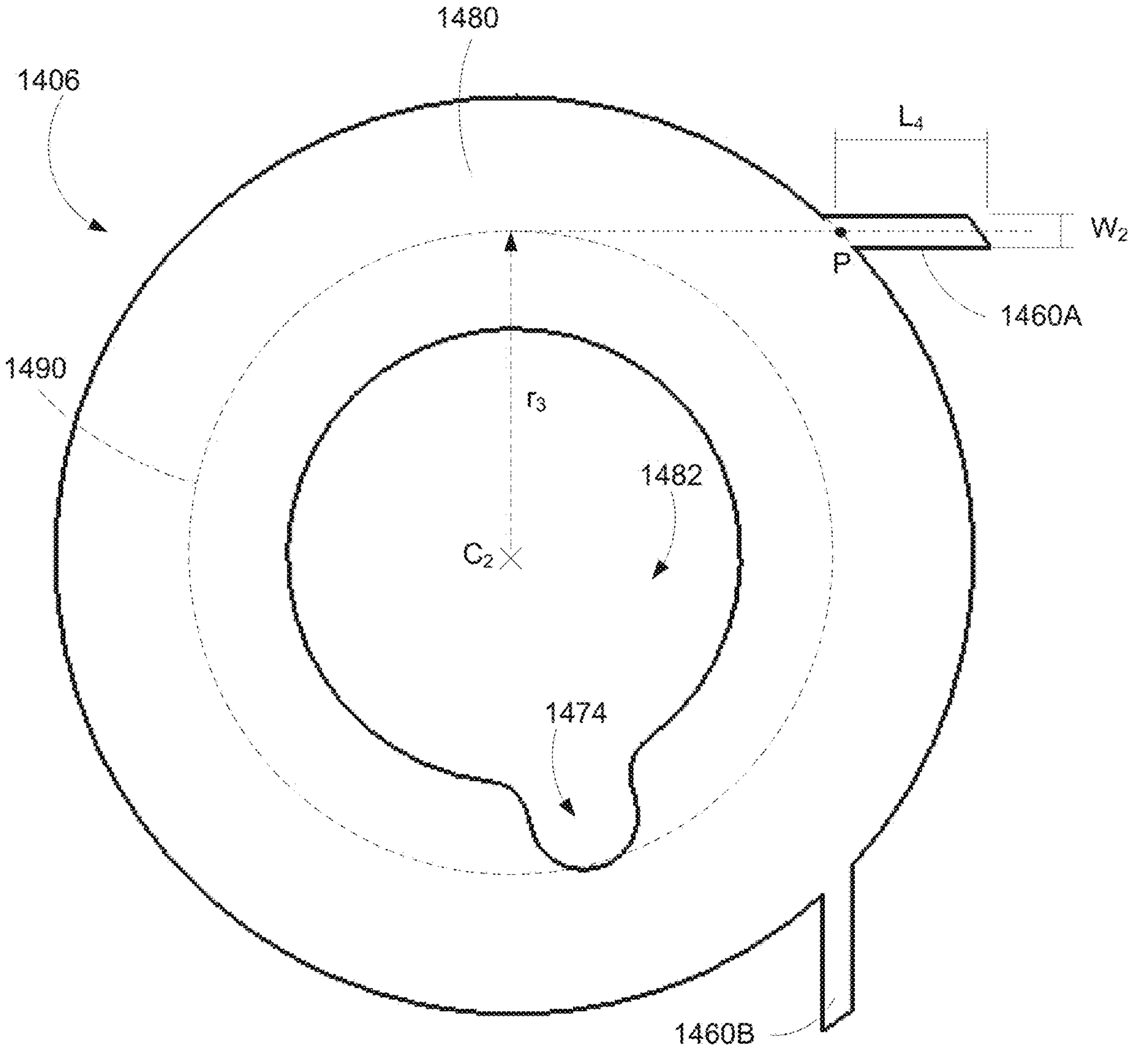
FIG. 17B-17C are distal and side elevation views, respectively, of the planar fixation feature of FIG. 17A, in accordance with an embodiment.
Figure 17C:

FIGS. 17A-17C illustrate the example shim 1406 in further detail. More specifically, FIG. 17A is an isometric view of the shim 1406, FIG. 17B is a distal view of the shim 1406, and FIG. 17C is a side elevation view of the shim 1406.

As illustrated in FIGS. 17A-17C, the shim 1406 includes a substantially circular body 1480 (although other shapes of shims are possible and contemplated) from which barbs 1460A-1460B extend. Each of the barbs 1460A-1460B extends in a counter-rotational direction opposite the primary helix 1405 of FIG. 14. The circular body 1480 further defines a through hole 1482 for coupling the shim 1406 to other components of a header assembly of a leadless biostimulator, such as the header assembly 1404 illustrated in FIG. 16. For example, the through hole 1482 may be shaped to receive a protrusion or extension of the header body 1470. As previously discussed, the edge of the through hole 1482 may further define a notch 1474 or a protrusion shaped to mate with a corresponding protrusion or notch, respectively, of the header body 1470. By doing so, the shim 1406 may be placed in a predetermined orientation relative to the header body 1470 during assembly.

The barbs 1460A-1460B of the shim 1406 may conform to a predetermined shape or arrangement and have a predetermined geometry. For example, as illustrated in FIG. 17B, each of the barbs 1460A-1460B extend outwardly from the circular body 1480 along a substantially straight path and terminate in a sharpened point. Referring to the barb 1460A, for example, the barb 1460A is offset from a center $C_2$ of the shim 1406 by a radius $r_3$ and extends perpendicular to the radius $r_3$ until the barb 1460A extends from the outer edge of the circular body 1480 by a barb length $L_4$. Phrased differently, the barb 1460A extends a distance of the barb length $L_4$ from a point P on the outer edge of the circular body 1480 and the point P corresponds to an intersection of the outer edge of the circular body 1480 and a line that is tangential to a circle 1490 defined by the radius $r_3$. As shown in FIG. 17B, the barb 1460A may be further defined by a barb width $W_2$. In certain example implementations, the radius $r_3$ may be from and including 0.030 inches to and including 0.090 inches, the barb length $L_4$ may be from and including 0.002 inches to and including 0.01 inches, and the barb width $W_2$ may be from and including 0.001 inches to and including 0.005 inches.

Although illustrated in FIGS. 17A-17C as being substantially straight, barbs of shims according to the present disclosure may have alternative shapes provided they extend from the circular body 1480 to resist counter rotation of a leadless pacemaker in which they are incorporated. For example and without limitation, such barbs may follow a circular curvate path or a spiraling curvate path. Also, while barbs 1460A-1460B are shown as extending substantially perpendicular to the radius $r_3$ from the outer edge of the circular body 1480, in other implementations, the barbs of the shim may instead extend at an angle from the outer edge of the circular body 1480 (e.g. from the point P from which the barb 1460A extends from the outer edge of the circular body 1480).

As illustrated in the preceding figures, the shim 1406 includes two barbs 1460A-1460B that are disposed on one side of the circular body 1480 and offset approximately 90 degrees from each other. In alternative implementations, however, the shim 1406 may include fewer or more than two barbs. For example and without limitation, implementations of shims according to the present disclosure may include from one to six or more arms. In implementations in which a shim includes multiple barbs, the barbs may be evenly or unevenly distributed about the circular body 1480. For example, in certain implementations, a second barb may be disposed at an offset from and including 90 degrees to and including 270 degrees relative to a first barb. Also, each barb may vary in its length and shape. For example and without limitation, some or all of the barbs of shims according to this disclosure may have different lengths, different widths, follow different curvatures, or have no curvature at all in the case of straight barbs.

As illustrated in FIG. 17C, the shim 1406 may be substantially flat and may be formed from a thin sheet of material. In certain implementations, the shim 1406 may be formed from a sheet or film having a thickness 1484 from and including 0.001 inches to and including 0.010 inches. For example, in one method of manufacturing the shim 1406, a sheet or film may be formed using a film converting process. The sheet/film may then be punched, cut, trimmed, or otherwise processed to produce the shim 1406.

To achieve the required characteristics of the barbs 1460A-1460B, the shim 1406 may be formed from a flexible plastic material, such as polyimide. In other implementations, the shim 1406 may instead be formed of other flexible biocompatible materials including, without limitation, one or more of one or more of polyester, polyethylene, polypropylene, polyurethane, polyether ether ketone (PEEK), or polyvinylidene fluoride. Material selection for the shim 1406 may alternatively be based on particular properties or characteristics of the material. In certain implementations, the shim may be formed from one or more bioabsorbable materials, as described above. For example, the bioabsorbable material(s) may include a magnesium alloy. In certain implementations, the shim 1406 may be formed from a material having a Young's modulus from and including 0.5 GPa to and including 10 GPa, Material selection for the shim may alternatively be based on material toughness which is often associated with specific tensile and compression strengths of the material.

E. Implantation of Biostimulators

Figure 18A:
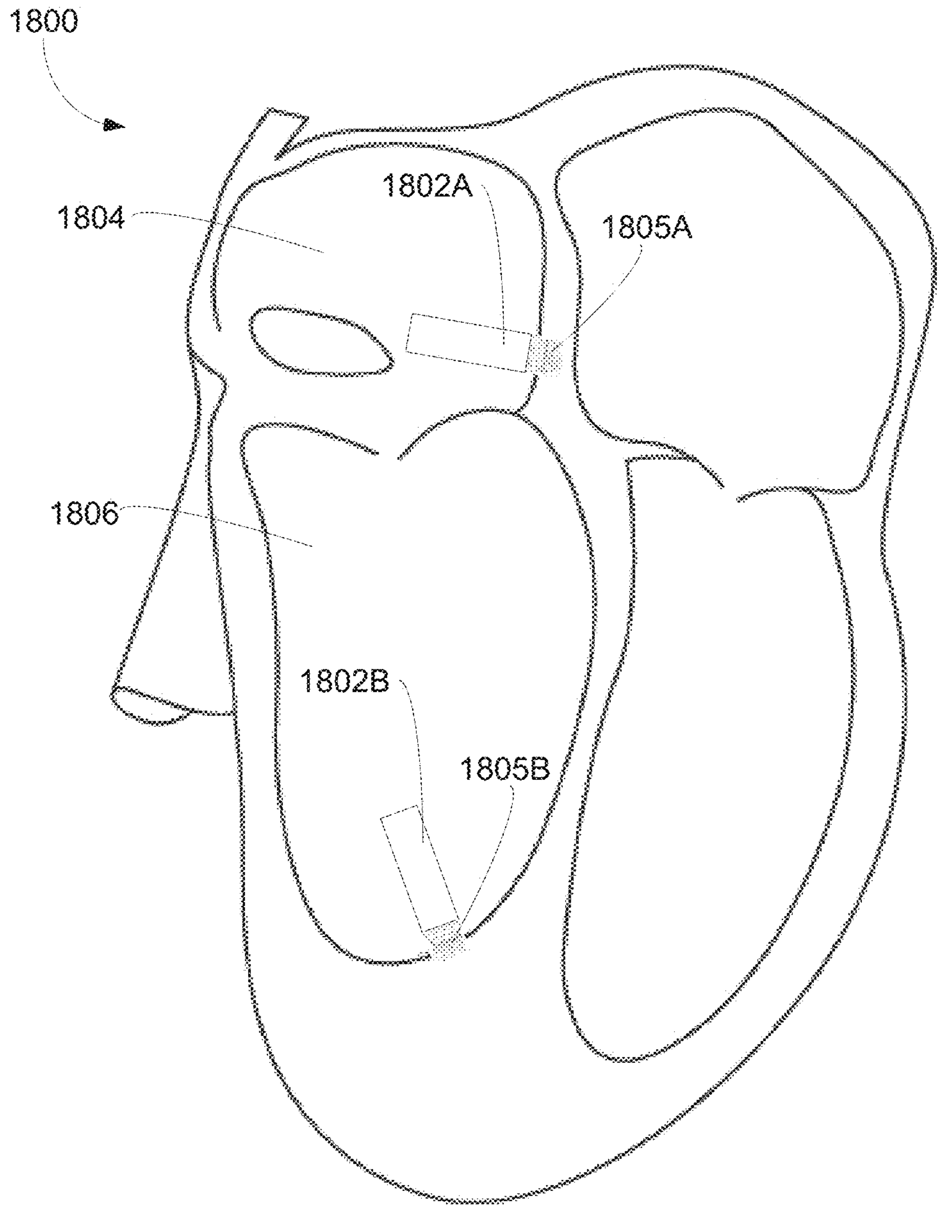
FIGS. 18A-18B are schematic illustrations of a patient heart in which biostimulators according to the present disclosure are fixed, in accordance with an embodiment.
Figure 18B:
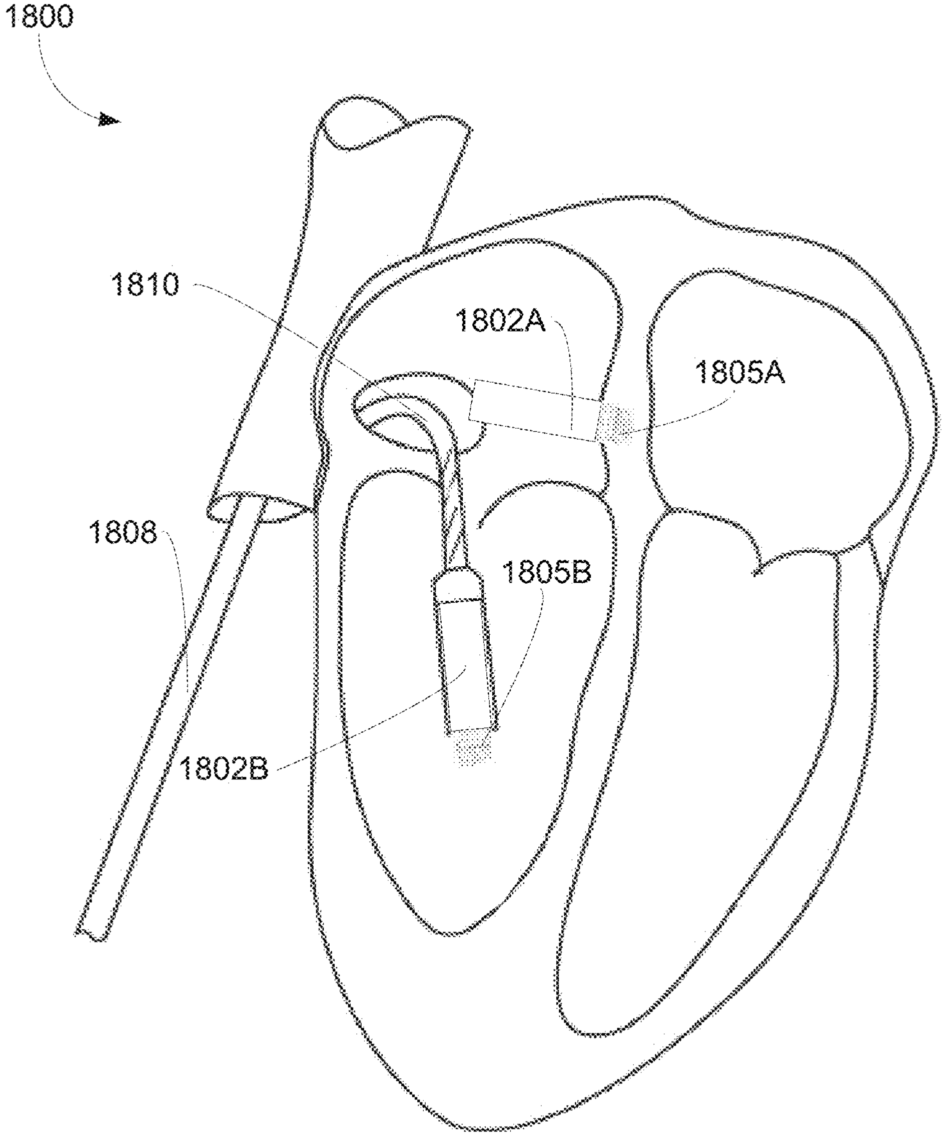

FIGS. 18A-18B illustrate endocardial implantation of biostimulators 1802A, 1802B in accordance within chambers of a patient heart 1800. As shown in FIG. 18A, a first biostimulator 1802A is implanted within an atrium 1804 of the heart 1800 while a second biostimulator 1802B is implanted within a ventricle 1806 of the heart 1800. Implantation of each of the first and second biostimulators 1802A, 1802B may be achieved, in part, by insertion of the biostimulators 1802A, 1802B endocardially through a guiding catheter. A torqueable catheter can be used to rotate the respective housings of the biostimulators 1802A, 1802B and force the respective primary fixation features 1805A, 1805B of the biostimulators 1802A, 1802B into corresponding heart tissue, affixing the primary fixation features 1805A, 1805B and corresponding electrodes into contact with stimulable tissue.

Similarly, and as illustrated in FIG. 18B, removal and retrieval of the biostimulators 1802A, 1802B may also be accomplished endocardially through a guiding catheter 1808. In the example of FIG. 18B, the second biostimulator 1802B is in the process of being removed from the heart 1800. To remove the second biostimulator 1802B, a torqueable catheter 1810 may be inserted into the heart 1800 through the guiding catheter 1808 and coupled to the biostimulator 1802B. The torqueable catheter 1810 may then be counter rotated to disengage the biostimulator 1802B. A similar process of inserting guide and torque catheters may also be used for epicardial fixation and removal of biostimulators in accordance with this disclosure.

For illustration purposes, the primary fixation features 1805A, 1805B are illustrated in FIGS. 18A and 18B as being helices extending from the distal ends of the biostimulators 1802A, 1802B. However, any primary fixation feature disclosed herein may be similarly implemented. For example, the biostimulators 1802A, 1802B may instead include any of the primary fixation features discussed in FIGS. 1-17C of the present disclosure.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A biostimulator, comprising:

a housing having a longitudinal axis and including an electronics compartment; and a fixation feature coupled to the housing, wherein the fixation feature includes a cylindrical body, a plurality of arms extending distally from the cylindrical body in a first screwing direction, and anti-rotation features extending from the plurality of arms in a second screwing direction, wherein the cylindrical body, the plurality of arms, and the anti-rotation features are contained within a tubular profile, and wherein the anti-rotation features extend from distal tips of the plurality of arms distal to the plurality of arms.

2. The biostimulator of claim 1, wherein the plurality of arms extend in the first screwing direction such that rotation of the fixation feature in the first screwing direction affixes the fixation feature to a heart.

3. The biostimulator of claim 2, wherein the anti-rotation features at the distal tips of the plurality of arms resist rotation of the fixation feature in the second screwing direction opposite to the first screwing direction when the fixation feature is affixed to the heart.

4. The biostimulator of claim 3, wherein the anti-rotation features include barbs extending from the distal tips.

5. The biostimulator of claim 4, wherein the barbs are formed from a material configured to yield to a predetermined counter torque to cause the fixation feature to disengage from the heart.

6. The biostimulator of claim 5, wherein the predetermined counter torque is greater than 0.5 oz-in.

7. The biostimulator of claim 1, wherein the cylindrical body is coupled to the housing.

8. A leadless pacemaker system, comprising:

a transport catheter; and a leadless cardiac pacemaker mounted on the transport catheter, wherein the leadless cardiac pacemaker includes a housing having a longitudinal axis and including an electronics compartment, and a fixation feature coupled to the housing, wherein the fixation feature includes a cylindrical body, a plurality of arms extending distally from the cylindrical body in a first screwing direction, and anti-rotation features extending from the plurality of arms in a second screwing direction, wherein the cylindrical body, the plurality of arms, and the anti-rotation features are contained within a tubular profile, and wherein the anti-rotation features extend from distal tips of the plurality of arms distal to the plurality of arms.

9. The leadless pacemaker system of claim 8, wherein the plurality of arms extend in the first screwing direction such that rotation of the fixation feature in the first screwing direction affixes the fixation feature to a heart.

10. The leadless pacemaker system of claim 9, wherein the anti-rotation features at the distal tips of the plurality of arms resist rotation of the fixation feature in the second screwing direction opposite to the first screwing direction when the fixation feature is affixed to the heart.

11. The leadless pacemaker system of claim 10, wherein the anti-rotation features include barbs extending from the distal tips.

12. The leadless pacemaker system of claim 11, wherein the barbs are formed from a material configured to yield to a predetermined counter torque to cause the fixation feature to disengage from the heart.

13. The leadless pacemaker system of claim 8, wherein the fixation feature is coupled to the housing.

14. A method of manufacturing a leadless biostimulator, comprising:

forming a fixation feature including a cylindrical body, a plurality of arms extending distally from the cylindrical body in a first screwing direction, and anti-rotation features extending from the plurality of arms in a second screwing direction; and mounting the fixation feature on a housing, wherein the housing has a longitudinal axis and includes an electronics compartment, wherein the cylindrical body, the plurality of arms, and the anti-rotation features are contained within a tubular profile, and wherein the anti-rotation features extend from distal tips of the plurality of arms distal to the plurality of arms.

15. The method of claim 14, wherein the plurality of arms extend in the first screwing direction such that rotation of the fixation feature in the first screwing direction affixes the fixation feature to a heart, and wherein the anti-rotation features include barbs extending in the second screwing direction opposite to the first screwing direction.

16. The method of claim 15, wherein the barbs are formed from a material configured to yield to a predetermined counter torque to cause the fixation feature to disengage from the heart.

17. The method of claim 14, wherein the cylindrical body is mounted on the housing.

* * * * *